(12) United States Patent
Mou et al.

(10) Patent No.: US 12,174,165 B2
(45) Date of Patent: Dec. 24, 2024

(54) MINIATURE GAS DETECTION SYSTEM

(71) Applicant: MICROJET TECHNOLOGY CO., LTD., Hsinchu (TW)

(72) Inventors: Hao-Jan Mou, Hsinchu (TW); Chin-Chuan Wu, Hsinchu (TW); Chieh-Yun Hsueh, Hsinchu (TW); Yung-Lung Han, Hsinchu (TW); Chi-Feng Huang, Hsinchu (TW); Tsung-I Lin, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 328 days.

(21) Appl. No.: 17/939,004

(22) Filed: Sep. 7, 2022

(65) Prior Publication Data
US 2023/0079257 A1 Mar. 16, 2023

(30) Foreign Application Priority Data
Sep. 10, 2021 (TW) ................... 110133820

(51) Int. Cl.
*G01N 33/00* (2006.01)
*B81B 3/00* (2006.01)
*G01N 1/22* (2006.01)

(52) U.S. Cl.
CPC ....... *G01N 33/0009* (2013.01); *B81B 3/0021* (2013.01); *G01N 1/2273* (2013.01); *B81B 2201/036* (2013.01)

(58) Field of Classification Search
CPC .......................... G01N 33/0009; G01N 1/2273
See application file for complete search history.

(56) References Cited

U.S. PATENT DOCUMENTS 9,990,381 B2 * 6/2018 Eltoukhy .............. C12Q 1/6874
2007/0281288 A1 * 12/2007 Belkin ................ G01N 21/6452
435/287.1

FOREIGN PATENT DOCUMENTS

| JP | 2020-180460 A | 11/2020 |
|----|---------------|---------|
| TW | 202001225 A | 1/2020 |
| TW | 202006332 A | 2/2020 |
| WO | 2021/129175 A1 | 7/2021 |

* cited by examiner

*Primary Examiner* — Kristina M Deherrera
*Assistant Examiner* — Jean F Morello
(74) *Attorney, Agent, or Firm* — Birch, Stewart, Kolasch & Birch, LLP

(57) ABSTRACT

A miniature gas detection system includes a separation flow channel fabricated by semiconductor processes and a filling material disposed in the main flow channel of the separation flow channel to perform adsorption and separation on compositions of compounds contained in the gas introduced into the main flow channel. Each detection flow channel is formed with a monitoring chamber, and a micro-electromechanical systems pump is formed on the bottom portion of the monitoring chamber. In each monitoring chamber, a light emitted from the light emitting element is reflected by the two mirrors and received by the light detection element. Therefore, the light detection elements obtain and output spectra of the compositions of compounds contained in the gas according to the differences in optical adsorptions of the compositions of compounds for lights with different wavelengths, so as to analyze and determine the type of the gas contained in the compositions of compounds.

19 Claims, 22 Drawing Sheets

MINIATURE GAS DETECTION SYSTEM

CROSS-REFERENCE TO RELATED APPLICATION

This non-provisional application claims priority under 35 U.S.C. § 119(a) to Patent Application No. 110133820 filed in Taiwan, R.O.C. on Sep. 10, 2021, the entire contents of which are hereby incorporated by reference.

BACKGROUND

Technical Field

The present disclosure relates to a miniature gas detection system, in particular, to a miniature gas detection system which is fabricated by semiconductor processes to detect compositions of compounds contained in the gas.

Related Art

One of the methods for gas analysis is gas chromatography (GC), which is a technique used in organic chemistry to separate and purify volatile, thermally stable compounds. Through the interaction between the mobile phase and the stationary phase in the system, the ingredients in the mixture flow at different flow rates, thereby achieving the separation of the ingredients.

However, at present, there are many models and types of gas chromatography meter in the market. Though these GC meters have different outlines and constructions, the GC meter typically contains the following basic systems: gas channel system, sample injection system, separation system, temperature control system, detection system, and record system. These GC meters have larger volumes because, in the separation system, a chromatography column is provided to perform the separation of the ingredients in the sample. The chromatography column is the core of the GC meter. Because the efficiency of the chromatography is related to the length, the inner diameter, the film thickness of the column, the longer the column is and the smaller the inner diameter, and the film thickness of the column is, the better the analysis effect is. As a result, the length of the column in the GC meter known to the inventor is generally very long, thus causing the column in the GC meter to occupy a lot of space.

Consequently, it is an issue of the present disclosure to provide a system to address the length of the column in the GC meter, to achieve chromatography for ingredients separation, and to replace the chromatography column in the GC meter, wherein the system can be used anytime and anywhere.

SUMMARY

One object of the present disclosure is to provide a miniature gas detection system including a separation flow channel and a filling material. The separation flow channel is fabricated by semiconductor processes and includes a main flow channel and a plurality of detection flow channels. The main flow channel guides a gas to do detection, and the plurality of detection flow channels is connected to the main flow channel. Each of the detection flow channels is formed with a monitoring chamber, a light emitting element is formed on one side of the monitoring chamber, and a light detection element is stacked and positioned on the light emitting element. Two mirrors are formed on two sides of the monitoring chamber and correspond to each other. A micro-electromechanical systems (MEMS) pump is formed on the bottom portion of the monitoring chamber. The filling material is disposed in the main flow channel of the separation flow channel to perform adsorption and separation of compositions of compounds contained in the gas introduced into the main flow channel. The compositions of compounds contained in the gas introduced into the main flow channel are adsorbed or separated by the filling material and presented at different regions of the main flow channel with different flow rates. When the MEMS pump of each of the detection flow channels is actuated, the compositions of compounds at different regions of the main flow channel are introduced into the monitoring chambers of the respective detection flow channels with a fixed amount. In the monitoring chamber of each of the detection flow channels, a light emitted from the light emitting element is illuminated on the two mirrors, reflected by the two mirrors, and received by the light detection element, so that the light detection elements in the respective monitoring chambers obtain and output spectra of the compositions of compounds contained in the gas according to the differences in optical adsorptions of the compositions of compounds for lights with different wavelengths, so as to analyze and determine the type of the gas contained in the compositions of compounds.

BRIEF DESCRIPTION OF THE DRAWINGS

The disclosure will become more fully understood from the detailed description given herein below, for illustration only and thus not limitative of the disclosure, wherein.

DETAILED DESCRIPTION

The present disclosure will now be described more specifically with reference to the following embodiments. It is to be noted that the following descriptions of different embodiments of this disclosure are presented herein for purpose of illustration and description only, and it is not intended to limit the scope of the present disclosure.

Figure 1A:
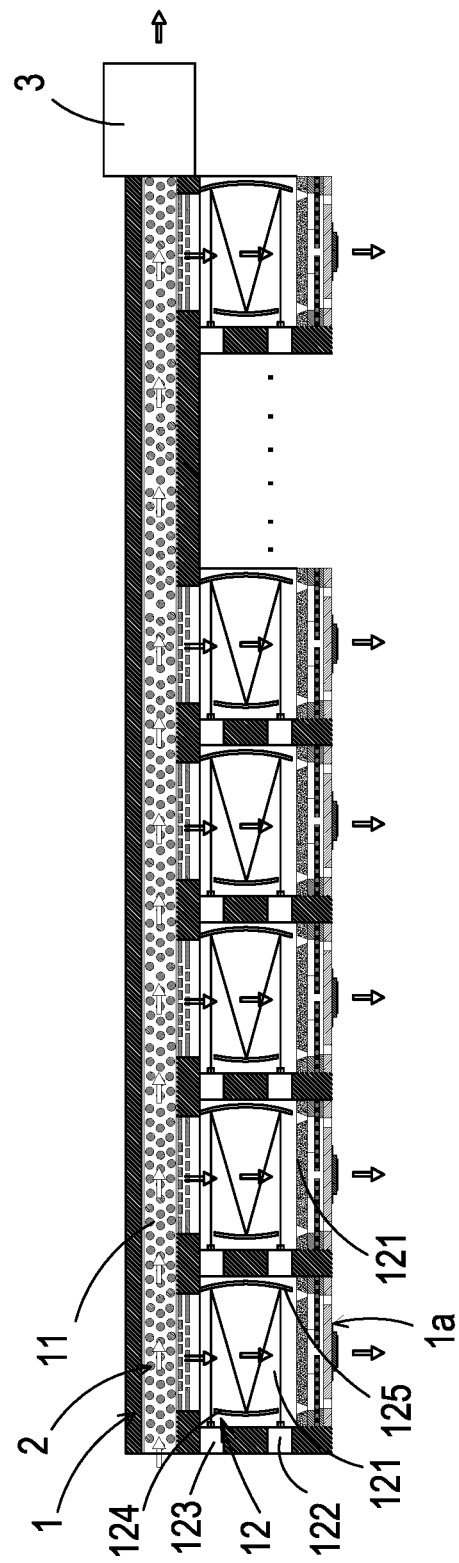
FIG. 1A and FIG. 1B illustrate schematic views of a miniature gas detection system of an exemplary embodiment in the present disclosure.

Please refer to FIG. 1A, according to one or some embodiments of the present disclosure, a miniature gas detection system is provided and includes a separation flow channel 1 and a filling material 2. The separation flow channel 1 is fabricated by semiconductor processes and includes a main flow channel 11 and a plurality of detection flow channels 12. The main flow channel 11 guides a gas for detection, and the plurality of detection flow channels 12 is connected to the main flow channel 11. Each of the detection flow channels 12 is formed with a monitoring chamber 121, a light emitting element 122 is on one side of the monitoring chamber 121, and a light detection element 123 is stacked and positioned on the light emitting element 122. Two mirrors 124, and 125 are formed on two sides of the monitoring chamber 121 and correspond to each other. A micro-electromechanical systems (MEMS) pump 1a is formed on the bottom portion of the monitoring chamber 121. Furthermore, the filling material 2 is disposed in the main flow channel 11 of the separation flow channel 1 to perform adsorption and separation of compositions of compounds contained in the gas introduced into the main flow channel 11. Hence, the compositions of compounds contained in the gas introduced into the main flow channel 11 are adsorbed or separated by the filling material 2 and presented at different regions of the main flow channel 11 with different flow rates. Moreover, when the MEMS pump 1a of each of the detection flow channels 12 is actuated, the compositions of compounds at different regions of the main flow channel 11 are introduced into the monitoring chambers 121 of the respective detection flow channels 12 with a fixed amount, and in the monitoring chamber 121 of each of the detection flow channels 12, a light emitted from the light emitting element 122 is illuminated on the two mirrors 124, 125, reflected by the two mirrors 124, 125, and received by the light detection element 123, so that the light detection elements 123 in the respective monitoring chambers 121 obtain and output spectra of the compositions of compounds contained in the gas according to the differences in optical adsorptions of the compositions of compounds for lights with different wavelengths, so as to analyze and determine the type of the gas contained in the compositions of compounds.

In one embodiment, the miniature gas detection system may further include a gas actuator 3. The gas actuator 3 is a small piezoelectric pump 3a connected to the main flow channel 11, the gas actuator 3 is actuated to guide the gas into the main flow channel 11 with a stable flow rate, so that the filling material 2 performs adsorption and separation on the compositions of compounds contained in the gas.

According to one or some embodiments of the present disclosure, in order to achieve the miniaturization of the separation flow channel 1 so as to reduce the size of the entire apparatus, the separation flow channel 1 is fabricated by semiconductor processes. The separation flow channel 1 includes a main flow channel 11 and a plurality of detection flow channels 12. It is noted that the number of the monitoring chambers 121 is in a range between 1 and 30; each of the monitoring chambers 121 is adapted to detect a compound contained in the gas, thus thirty monitoring chambers 121 can detect thirty different compositions of compounds contained in the gas, but not limited thereto. A length of each of the monitoring chambers 121 connected to the main flow channel 11 is in a range between 0.8 mm (800 μm) and 2 mm, and a length of the main flow channel 11 is in a range between 2 mm and 24 mm, but not limited thereto. Alternatively, in some embodiments, the length of each of the monitoring chambers 121 connected to the main flow channel 11 is in a range between 800 nm and 2 μm, and the length of the main flow channel 11 is in a range between 2 μm and 24 μm. In this embodiment, the length of the main flow channel 11 may be adjusted correspondingly depending on whether the length of the monitoring chamber 121 is of a millimeter scale, a micrometer scale, or a nanometer scale. As above, the number of the monitoring chambers 121 can be adjusted according to different design requirements, and the length of the monitoring chamber 121 may be of a millimeter scale, a micrometer scale, or a nanometer scale. Moreover, the number of the monitoring chambers 121 is in a range between 1 and 30, thus the number of the MEMS pumps 1a formed in the monitoring chambers 121 is also in a range between 1 and 30, but not limited thereto. The number of the MEMS pumps 1a is equal to the number of the monitoring chambers 121, thus the scale of the MEMS pumps 1a is also corresponding to the scale of the monitoring chambers 121 of the detection flow channels 12.

Figure 1B:
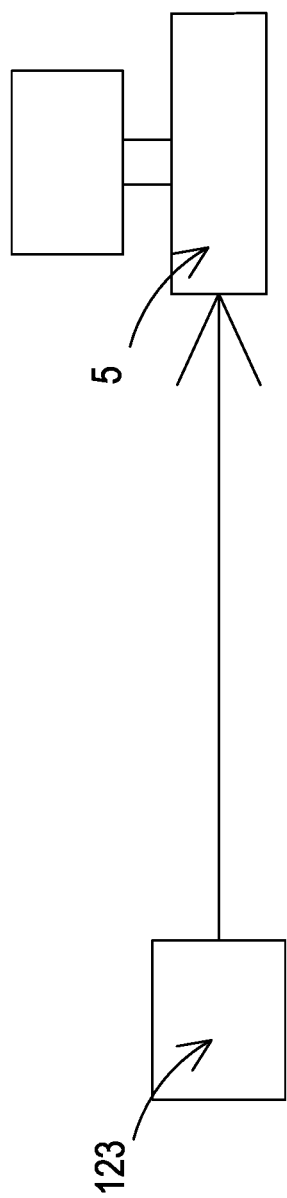

Please refer to FIG. 1B. Data of the spectra of the compositions of compounds received and obtained by the light detection elements 123 are outputted to an external computer system 5, so that the external computer system 5 performs data capture, data storage, and data analysis on the data of the spectra, so as to analyze and determine the type of the gas contained in the compositions of compounds. It is noted that the data of the spectra of the compositions of compounds obtained by the light detection element 123 are resulted from the compound contained in the gas in the monitoring chambers 121 of each of the detection flow channels 12, and the light detection element 123 obtains data of the spectra of the compositions of compounds after the light emitted from the light emitting element 122 illuminates on the gas in the monitoring chamber 121, reflected by the two mirrors 124, 125, and received by the light detection element 123.

Figure 2A:
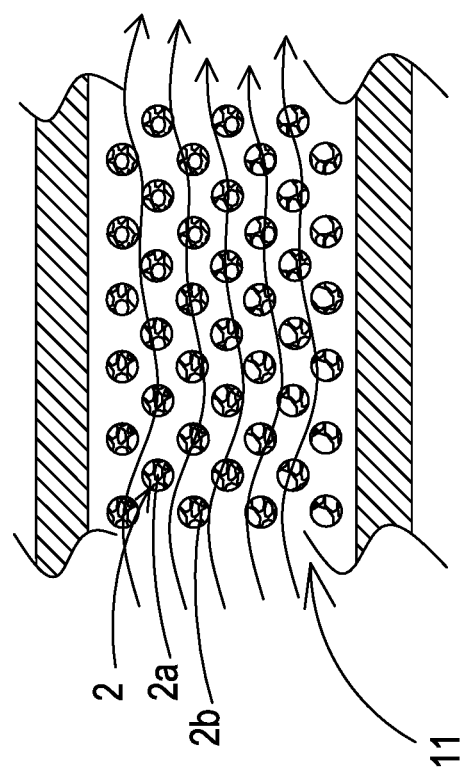
FIG. 2A to FIG. 2C illustrate schematic views of a filling material in the main flow channel of the miniature gas detection system of the exemplary embodiment in the present disclosure.
Figure 2B:
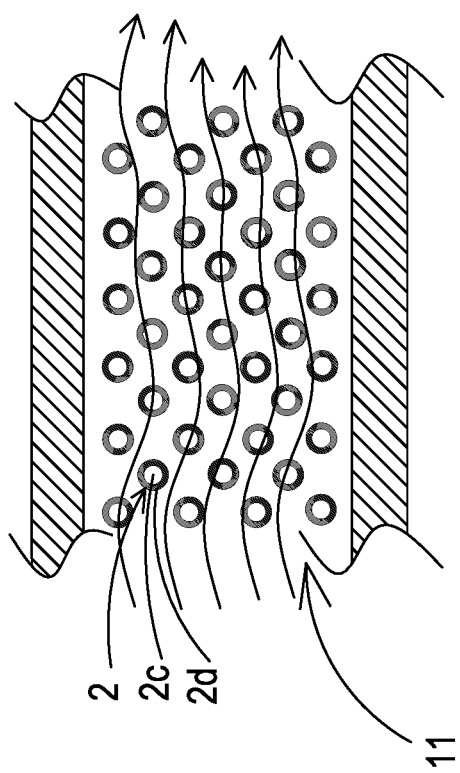
Figure 2C:
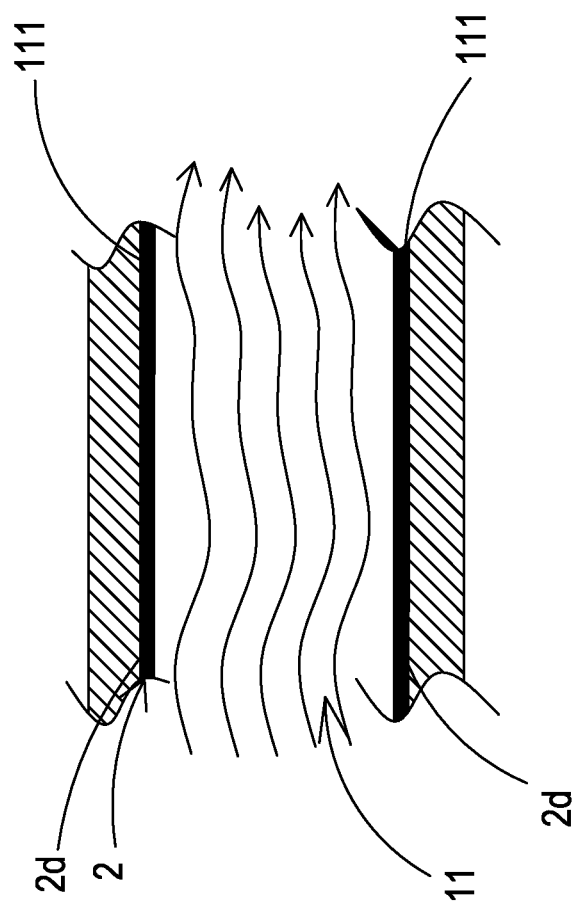

Please refer to FIG. 2A to FIG. 2C. In the miniature gas detection system of one embodiment of the present disclosure, the gas is introduced into the main flow channel 11, and the compositions of compounds contained in the gas are adsorbed or separated by the filling material 2 and presented at different regions of the main flow channel 11 with different flow rates. The filling material 2 is a porous polymer 2a which is adsorptive, and the filling material 2 is filled in the main flow channel 11. In some other embodiments, the filling material 2 is a molecular sieve material 2b which is adsorptive, and the filling material 2 is filled in the main flow channel 11. The filling material 2 may be a filling substrate 2c uniformly covered by a fixed liquid film 2d which is adsorptive, and the filling material 2 is filled in the main flow channel 11. The filling material 2 may be an oxide of silicon, and the surface of the filling material 2 has hydroxyl groups for implanting the fixed liquid film 2d on the surface of the filling material 2. The filling material 2 may be a fixed liquid film 2d directly coated on an inner surface 111 of the main flow channel 11. The filling material 2 may be a fixed liquid film 2d directly sputtered on an inner surface 111 of the main flow channel 11.

Figure 3A:
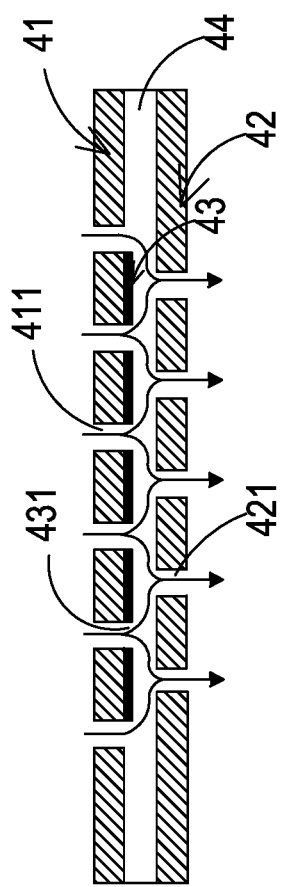
FIG. 3A and FIG. 3B illustrate schematic views showing the open condition and the close condition of a valve element of the miniature gas detection system of the exemplary embodiment in the present disclosure.
Figure 3B:
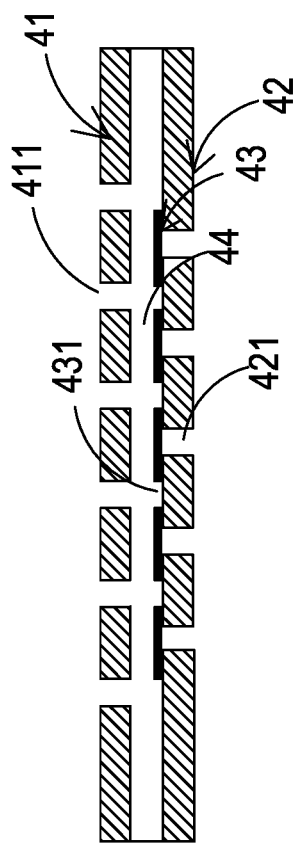

Please refer to FIG. 3A and FIG. 3B. A valve element 4 is formed at a communication portion between each of the detection flow channels 12 and the main flow channel 11. The valve element 4 includes an upper base layer 41, a lower base layer 42, and a valve layer 43. The valve layer 43 is in a receiving space 44 between the upper base layer 41 and the lower base layer 42. A plurality of ventilation holes 411, 421, and 431 are respectively formed on the upper base layer 41, the lower base layer 42, and the valve layer 43. The ventilation holes 411 of the upper base layer 41 and the ventilation holes 431 of the valve layer 43 are substantially aligned with each other, and the ventilation holes 421 of the lower base layer 42 and the ventilation holes 411 of the upper base layer 41 are not aligned with each other. The valve layer 43 is a charged material, and the upper base layer 41 is a conductive material with bipolarity. Thus, when the valve layer 43 and the upper base layer 41 are of different polarities, the valve layer 43 is moved toward the upper base layer 41, so that the valve element 4 is opened; when the valve layer 43 and the upper base layer 41 are of the same polarity, the valve layer 43 is moved toward the lower base layer 42, so that the valve element 4 is closed.

Please refer to FIG. 1 and FIG. 4A to FIG. 5D. In one embodiment, the gas actuator 3 is a piezoelectric pump 3a, and the piezoelectric pump 3a includes an inlet plate 31a, a resonance sheet 32a, and a piezoelectric actuator 33a. The inlet plate 31a has at least one inlet hole 311a, at least one convergence channel 312a, and a convergence chamber 313a. The at least one inlet hole 311a is used to introduce the gas into the piezoelectric pump 3a, and the at least one inlet hole 311 correspondingly penetrates into the at least one convergence channel 312a. The at least one convergence channel 312a is converged into the convergence chamber 313a, so that the gas introduced from the at least one inlet hole 311a is converged into the convergence chamber 313a. The resonance sheet 32a is attached to the inlet plate 31a. The resonance sheet 32a has a perforation 321a, a movable portion 322a, and a fixed portion 323a. The perforation 321a is located at a central portion of the resonance sheet 32a and corresponds to the convergence chamber 313a of the inlet plate 31a. The movable portion 322a is disposed at a periphery of the perforation 321a and is disposed at a portion corresponding to the convergence chamber 313a, and the fixed portion 323a is disposed at an outer periphery of the resonance sheet 32a and attached to the inlet plate 31a. The piezoelectric actuator 33a is attached to the resonance sheet 32a and disposed correspondingly to the resonance sheet 32a. The piezoelectric actuator 33a includes a suspension plate 331a, an outer frame 332a, at least one supporting element 333a, and a piezoelectric element 334a. The suspension plate 331a is of a square shape and capable of bending and vibrating. The outer frame 332a is disposed around a periphery of the suspension plate 331a. The at least one supporting element 333a is formed between the suspension plate 331a and the outer frame 332a to provide flexible support for the suspension plate 331a. The piezoelectric element 334a has a side length, the side length of the piezoelectric element 334a is smaller than or equal to the side length of the suspension plate 331a, and the piezoelectric element 334a is attached to a surface of the suspension plate 331a so as to drive the suspension plate 331a to bend and vibrate when the piezoelectric element 334a is applied with a voltage. A chamber space 37a is between the resonance sheet 32a and the piezoelectric actuator 33a, so that when the piezoelectric actuator 33a is driven, the gas outside the piezoelectric pump 3a is introduced into the piezoelectric pump 3a through the at least one inlet hole 311a of the inlet plate 31a, converged into the convergence chamber 313a via the at least one convergence channel 312a, flowed through the perforation 321a of the resonance sheet 32a, and transmitted outwardly by a resonance effect resulting between the piezoelectric actuator 33a and the movable portion 322a of the resonance sheet 32a. The piezoelectric pump 3a further includes a first insulation sheet 34a, a conductive sheet 35a, and a second insulation sheet 36a. The inlet plate 31a, the resonance sheet 32a, the piezoelectric actuator 33a, the first insulation sheet 34a, the conductive sheet 35a, and the second insulation sheet 36a are sequentially stacked and assembled.

Figure 4A:
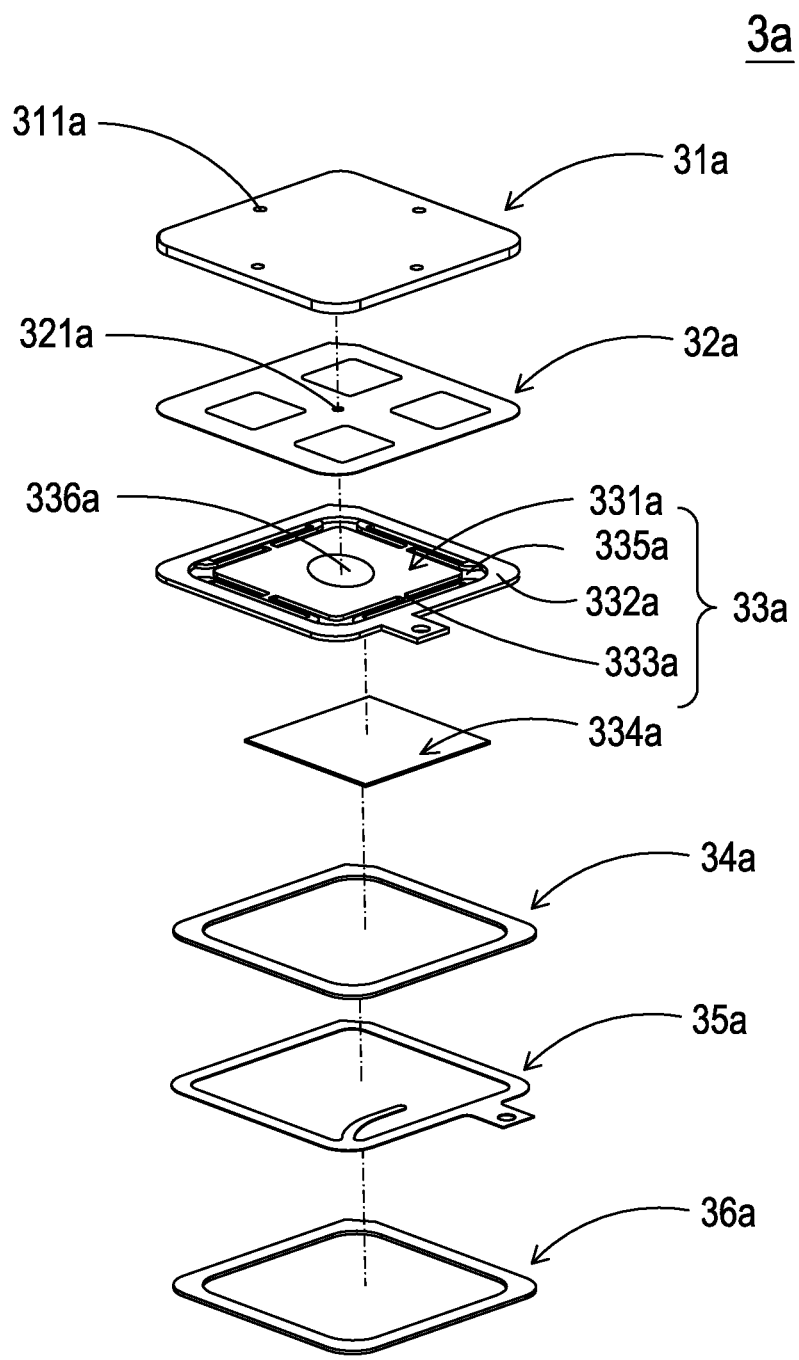
FIG. 4A illustrates an exploded view of a piezoelectric pump of the miniature gas detection system of the exemplary embodiment in the present disclosure.
Figure 4B:
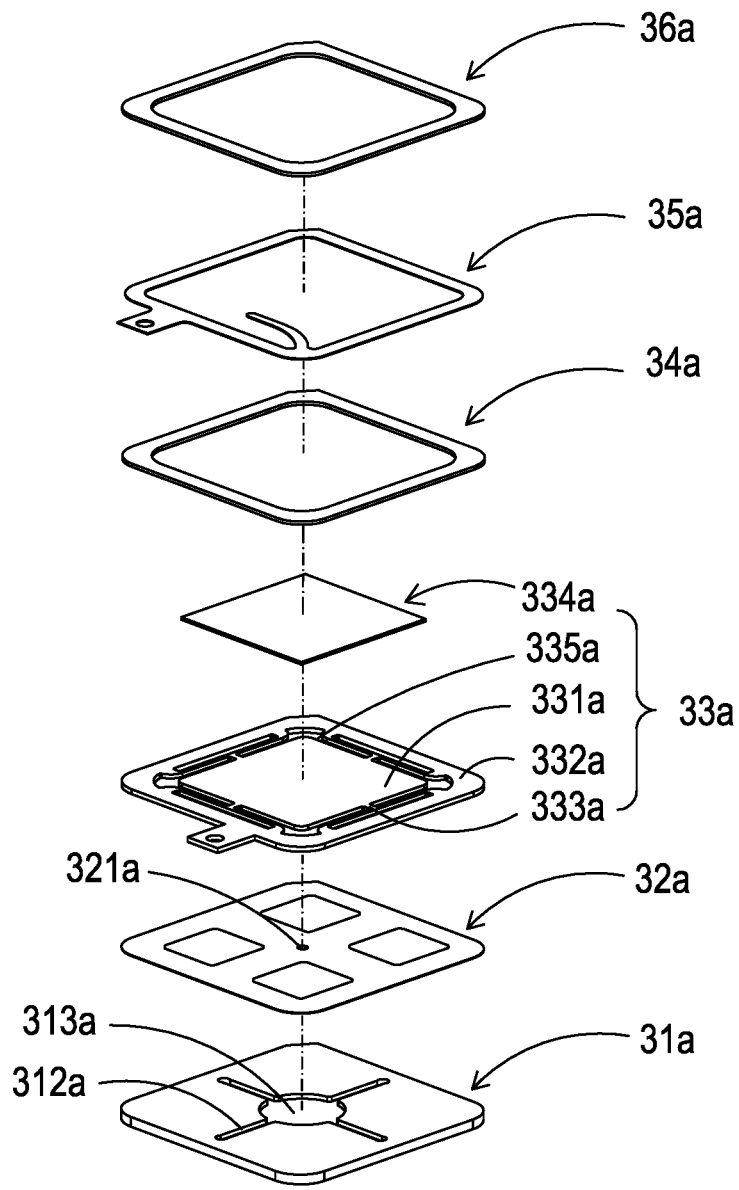
FIG. 4B illustrates an exploded view of the piezoelectric pump of the miniature gas detection system of the exemplary embodiment in the present disclosure.

Please refer to FIG. 4A and FIG. 4B. The piezoelectric pump 3a includes an inlet plate 31a, a resonance sheet 32a, a piezoelectric actuator 33a, a first insulation sheet 34a, a conductive sheet 35a, and a second insulation sheet 36a which are sequentially stacked and assembled. The inlet plate 31a has at least one inlet hole 311a, at least one convergence channel 312a, and a convergence chamber 313a. The inlet hole 311a is used to introduce the gas into the piezoelectric pump 3a. The at least one inlet hole 311a correspondingly penetrates into the at least one convergence channel 312a, and the at least one convergence channel 312a is converged into the convergence chamber 313a, so that the gas introduced from the at least one inlet hole 311a can be converged into the convergence chamber 313a. In this embodiment, the number of the inlet holes 311a and the number of the convergence channels 312a are the same. Moreover, in this embodiment, the number of the inlet holes 311a and the number of the convergence channels 312a both are exemplified by four, respectively, but not limited thereto. The four inlet holes 311a respectively penetrate into the four convergence channels 312a, and the four convergence channels 312a are converged into the convergence chamber 313a.

Figure 5A:
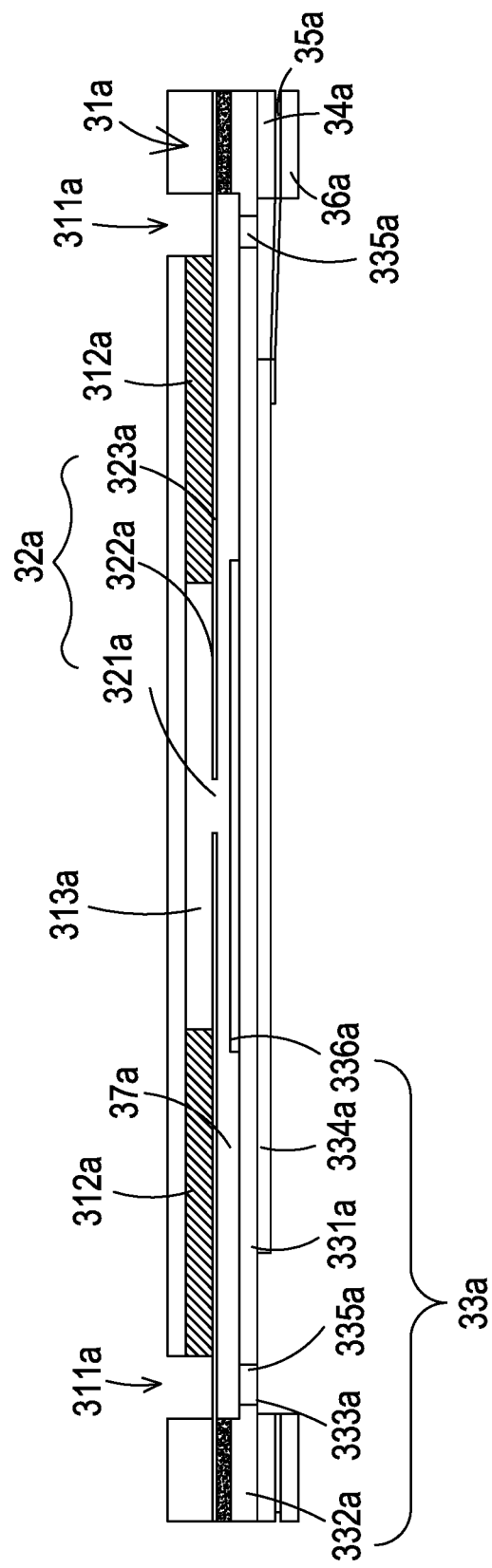
FIG. 5A illustrates a cross-sectional view of the piezoelectric pump of the miniature gas detection system of the exemplary embodiment in the present disclosure.

Please refer to FIG. 4A, FIG. 4B, and FIG. 5A. The resonance sheet 32a may be attached to and assembled on the inlet plate 31a. Furthermore, the resonance sheet 32a has a perforation 321a, a movable portion 322a, and a fixed portion 323a. The perforation 321a is located at a central portion of the resonance sheet 32a and corresponds to the convergence chamber 313a of the inlet plate 31a. The movable portion 322a is disposed at a periphery of the perforation 321a and is disposed at a portion corresponding to the convergence chamber 313a. The fixed portion 323a is disposed at an outer periphery of the resonance sheet 32a and attached to the inlet plate 31a.

Please still refer to FIG. 4A, FIG. 4B, and FIG. 5A. The piezoelectric actuator 33a attached to and disposed correspondingly to the resonance sheet 32a includes a suspension plate 331a, an outer frame 332a, at least one supporting element 333a, a piezoelectric element 334a, at least one gap 335a, and a protruding portion 336a. In the embodiments of the present disclosure, the suspension plate 331a is of a square shape. It is noted that, the reason why the suspension plate 331a adopts the square shape is that, compared with a circle suspension plate having a diameter equal to the side length of the square suspension plate 331a, the square suspension plate 331a has the advantage of saving electric power. The power consumption of a capacitive load operated at a resonance frequency may increase as the resonance frequency increases, and since the resonance frequency of a square suspension plate 331a is much lower than the resonance frequency of a circular suspension plate, the power consumption of the square suspension plate 331a is relatively low as well. Consequently, the square design of the suspension plate 331a used in one or some embodiments of the present disclosure has the benefit of power saving. In the embodiments of the present disclosure, the outer frame 332a is disposed around the periphery of the suspension plate 331a. The at least one supporting element 333a is formed between the suspension plate 331a and the outer frame 332a to provide a flexible support for the suspension plate 331a. In the embodiments of the present disclosure, the piezoelectric element 334a has a side length, which is shorter than or equal to the side length of the suspension plate 331a. The piezoelectric element 334a is attached to the surface of the suspension plate 331a so as to drive the suspension plate 331a to bend and vibrate when the piezoelectric element 334a is applied with a voltage. There is at least one gap 335a formed between the suspension plate 331a, the outer frame 332a, and the at least one supporting element 333a for the gas to flow therethrough. The protruding portion 336a is disposed on the surface of the suspension plate 331a opposite to the surface of the suspension plate 3331a where the piezoelectric element 334a is attached. In this embodiment, the protruding portion 336a may be a convex structure that protrudes out from and is integrally formed with the surface of the suspension plate 331a opposite to the surface of the suspension plate 331a where the piezoelectric element 334a is attached by performing an etching process on the suspension plate 331a.

In this embodiment, the inlet plate 31a, the resonance sheet 32a, the piezoelectric actuator 33a, the first insulation plate 34a, the conductive plate 35a, and the second insulation plate 36a are sequentially stacked and assembled, and a chamber space 37a is formed between the suspension plate 331a of the piezoelectric actuator 33a and the resonance sheet 32a. The chamber space 37a can be formed by filling material, such as conductive adhesive, in the space between the resonance sheet 32a and the outer frame 332a of the piezoelectric actuator 33a, but not limited thereto, thereby maintaining a certain distance between the resonance sheet 32a and a surface of the suspension plate 331a to form the chamber space 37a so as to allow the gas to be guided to and flow more quickly. Further, since an appropriate distance is maintained between the suspension plate 331a and the resonance sheet 32a, the interference raised by the contact between the suspension plate 331a and the resonance sheet 32a can be reduced, so that the noise generated thereby can be reduced as well. In other embodiments, the required thickness of filling the conductive adhesive between the resonance sheet 32a and the outer frame 332a of the piezoelectric actuator 33a can be decreased by increasing the height of the outer frame 332a of the piezoelectric actuator 33a. Accordingly, the entire structure of the piezoelectric pump 3a would not be indirectly affected since the filling material of conductive adhesive might be influenced by the hot pressing temperature and the cooling temperature, thereby avoiding the situation that the actual spacing of the chamber space 37a is affected by the thermal expansion and contraction of the filling material of the conductive adhesive, but not limited thereto. Moreover, the height of the chamber space 37a also affects the transmission efficiency of the piezoelectric pump 3a. Therefore, it is important to maintain a fixed height of the chamber space 37a to achieve stable transmission efficiency of the piezoelectric pump 3a.

Figure 5B:
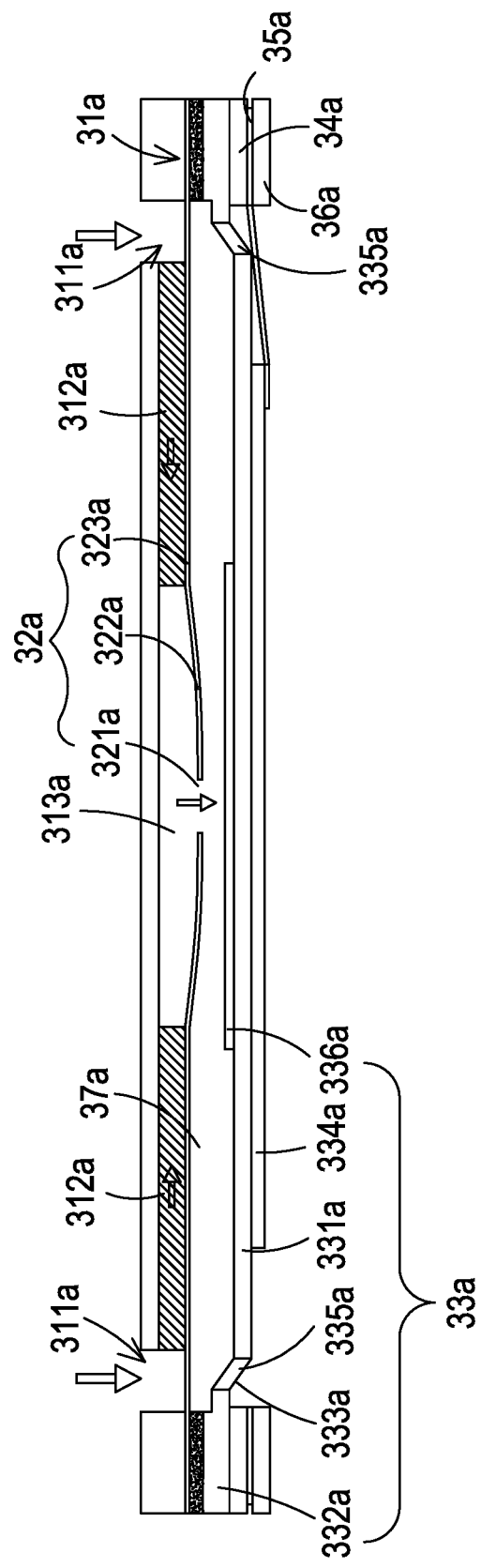
FIG. 5B to FIG. 5D illustrate cross-sectional views showing the operation steps of the piezoelectric pump of the miniature gas detection system of the exemplary embodiment in the present disclosure.
Figure 5C:
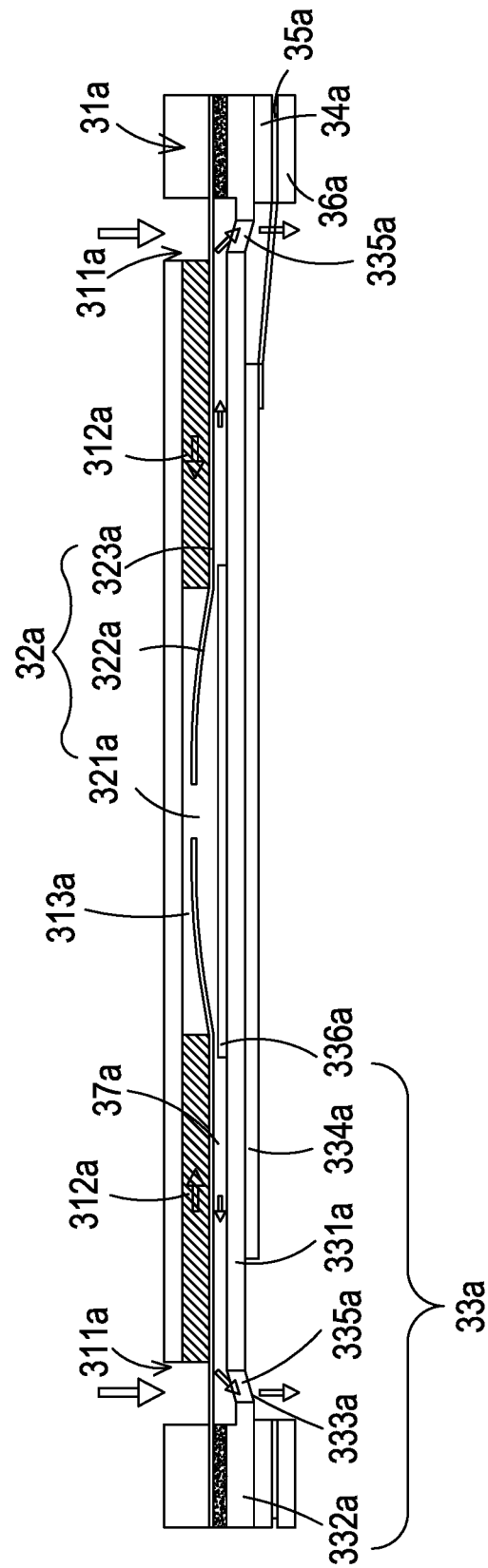
Figure 5D:
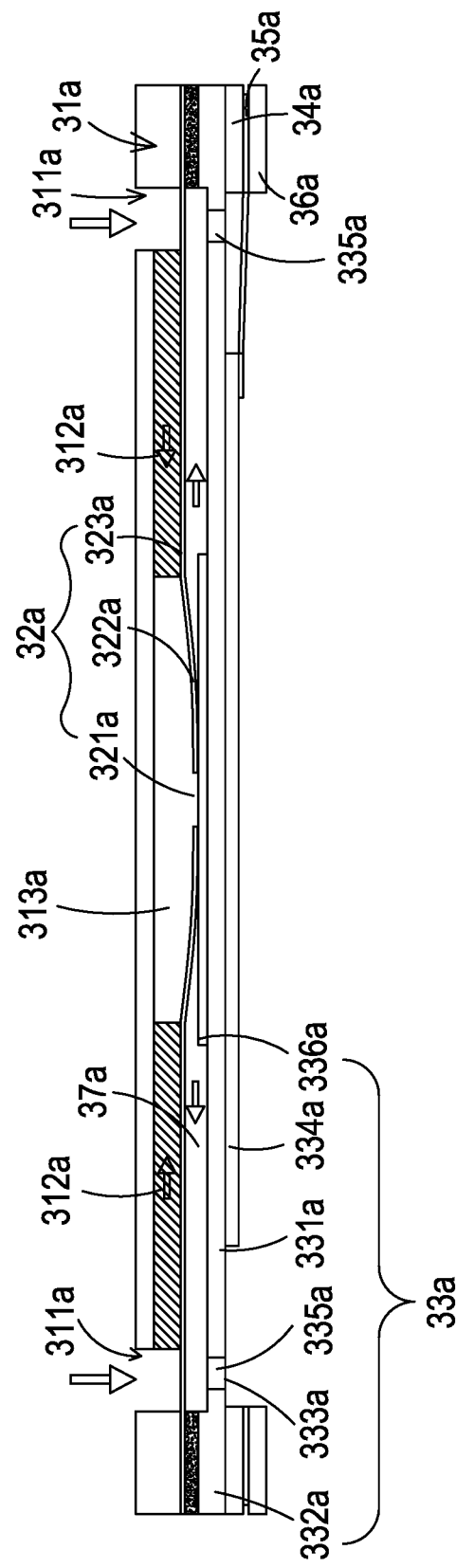

In order to understand the operation steps of the aforementioned piezoelectric pump 3a in the gas transmitting procedure, please refer to FIG. 5B to FIG. 5D. Please refer to FIG. 5B first, the piezoelectric element 334a of the piezoelectric actuator 33a deforms after being applied with a driving voltage, and the piezoelectric element 334a drives the suspension plate 331a to move downwardly and to move away from the inlet plate 31a. Thus, the volume of the chamber space 37a is increased and negative pressure is generated inside the chamber space 37a, thereby drawing the gas into the convergence chamber 313a and entering the chamber space 37a. At the same time, owing to the resonance effect, the resonance sheet 32a moves downwardly and moves away from the inlet plate 31a at the same time, and increases the volume of the convergence chamber 313a. Furthermore, since the gas inside the convergence chamber 313a is drawn into the chamber space 37a, the convergence chamber 313a is in a negative pressure state as well, and the gas can be drawn into the convergence chamber 313a through the inlet hole 311a, and the convergence channel 312a. Then, please refer to FIG. 5C. The piezoelectric element 334a drives the suspension plate 331a to move upwardly to move toward the inlet plate 31a and compresses the chamber space 37a. Similarly, since the resonance sheet 32a resonates with the suspension plate 331a, the resonance sheet 32a also moves upwardly and moves toward the inlet plate 31a, thereby pushing the gas in the chamber space 37a to move downwardly and transmit out of the piezoelectric pump 3a through the at least one gap 335a so as to achieve gas transmission. Last but not least, please refer to FIG. 5D. When the suspension plate 331a moves resiliently to its original position, the resonance sheet 32a still moves downwardly and moves away from the inlet plate 31a due to its inertia momentum. At this time, the resonance sheet 32a compresses the chamber space 37a, so that the gas in the chamber space 37a is moved toward the gap 335a and the volume of the convergence chamber 313a is increased. Accordingly, the gas can be drawn into the convergence chamber 313a continuously through the inlet holes 311a and the convergence channels 312a and can be converged at the convergence chamber 313a. Through continuously repeating the operation steps of the piezoelectric pump 3a shown in FIG. 5B to FIG. 5D, the piezoelectric pump 3a can make the gas continuously enter the flow paths formed by the inlet plate 31a and the resonance sheet 32a from the inlet holes 311a, thereby generating a pressure gradient. The gas is then transmitted outward through the gap 335a. As a result, the gas can flow at a relatively high speed, thereby achieving the gas transmission with the piezoelectric pump 3a.

Please refer to FIG. 1 and FIG. 6A to FIG. 6D. In one embodiment, the gas actuator 3 is a piezoelectric blower pump 3b, and the piezoelectric blower pump 3b includes a nozzle plate 31b, a chamber frame 32b, an actuation body 33b, an insulation frame 34b, and a conductive frame 35b. The nozzle plate 31b includes a suspension sheet 311b and a hollow hole 312b. The suspension sheet 311b is capable of bending and vibrating, and the hollow hole 312b is formed at a central portion of the suspension sheet 311b. The chamber frame 32b is stacked on the suspension sheet 311b. The actuation body 33b is stacked on the chamber frame 32b. The actuation body 33b includes a piezoelectric carrying plate 331b, an adjusting resonance plate 332b, and a piezoelectric plate 333b. The piezoelectric carrying plate 331b is stacked on the chamber frame 32b, the adjusting resonance plate 332b is stacked on the piezoelectric carrying plate 331b, and the piezoelectric plate 333b is stacked on the adjusting resonance plate 332b so as to drive the piezoelectric carrying plate 331*b* and the adjusting resonance plate 332*b* to bend and vibrate reciprocatingly when the piezoelectric plate 333*b* is applied with a voltage. The insulation frame 34*b* is stacked on the actuation body 33*b*. The conductive frame 35*b* is stacked on the insulation frame 34*b*. The nozzle plate 31*b* is fixed, so that a clearance is defined outside the nozzle plate 31*b* for the gas to flow therethrough; a gas flow chamber is formed at the bottom portion of the nozzle plate 31*b*, and a resonance chamber 36*b* is formed among the actuation body 33*b*, the chamber frame 32*b*, and the suspension sheet 311*b*. The nozzle plate 31*b* is capable of being driven to move correspondingly by driving the actuation body 33*b*, so that the suspension sheet 311*b* of the nozzle plate 31*b* vibrates reciprocatingly, and thus the gas enters the gas flow chamber through the gap and then is discharged out of the gas flow chamber, thereby achieving a gas transmission.

Please refer to FIG. 6A to FIG. 6D, the piezoelectric blower pump 3*b* includes a nozzle plate 31*b*, a chamber frame 32*b*, an actuation body 33*b*, an insulation frame 34*b*, and a conductive frame 35*b*. The nozzle plate 31*b* is made of a flexible material and has a suspension sheet 311*b* and a hollow hole 312*b*. The suspension sheet 311*b* is a flexible sheet that can bend and vibrate. The hollow hole 312*b* penetrates through the central portion of the suspension sheet 311*b* for the air flowing therethrough. In one embodiment of the present disclosure, the shape of the suspension sheet 311*b* can be selected from square, circle, ellipse, triangle, or polygon.

Figure 6A:
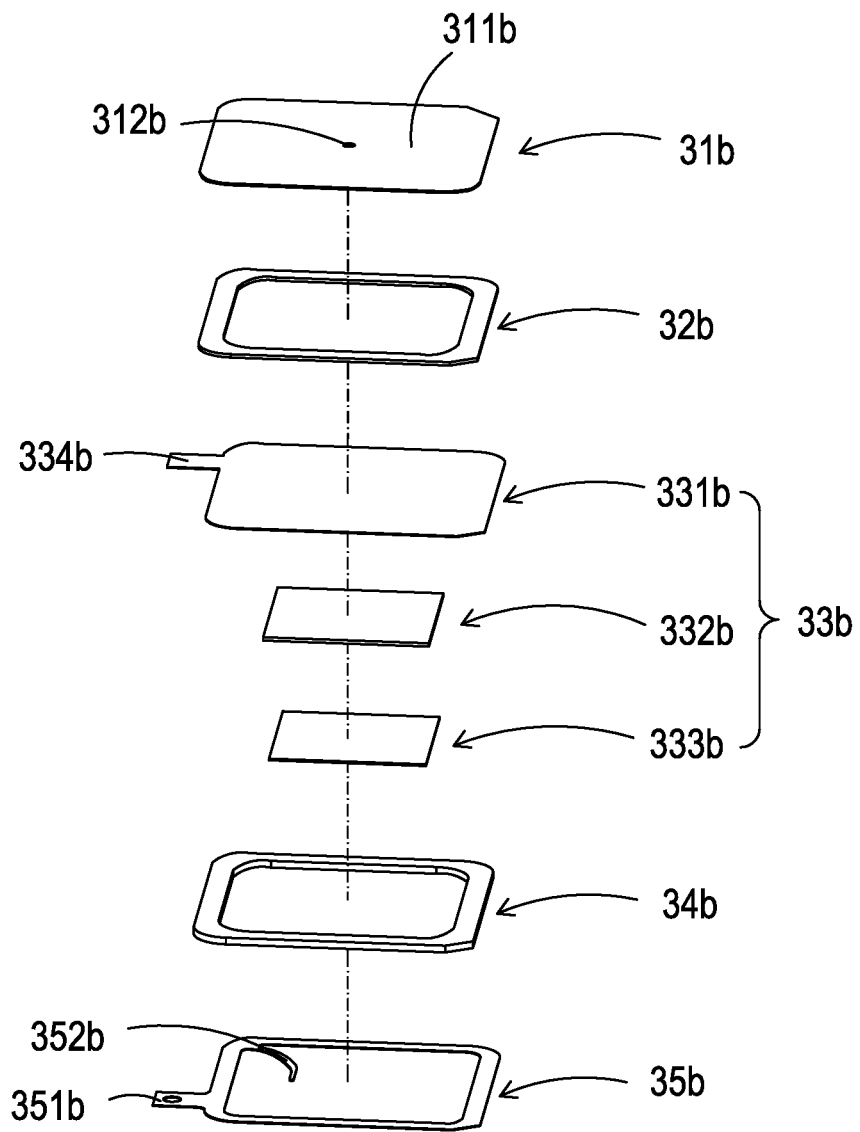
FIG. 6A illustrates an exploded view of a piezoelectric blower pump of the miniature gas detection system of the exemplary embodiment in the present disclosure.
Figure 6B:
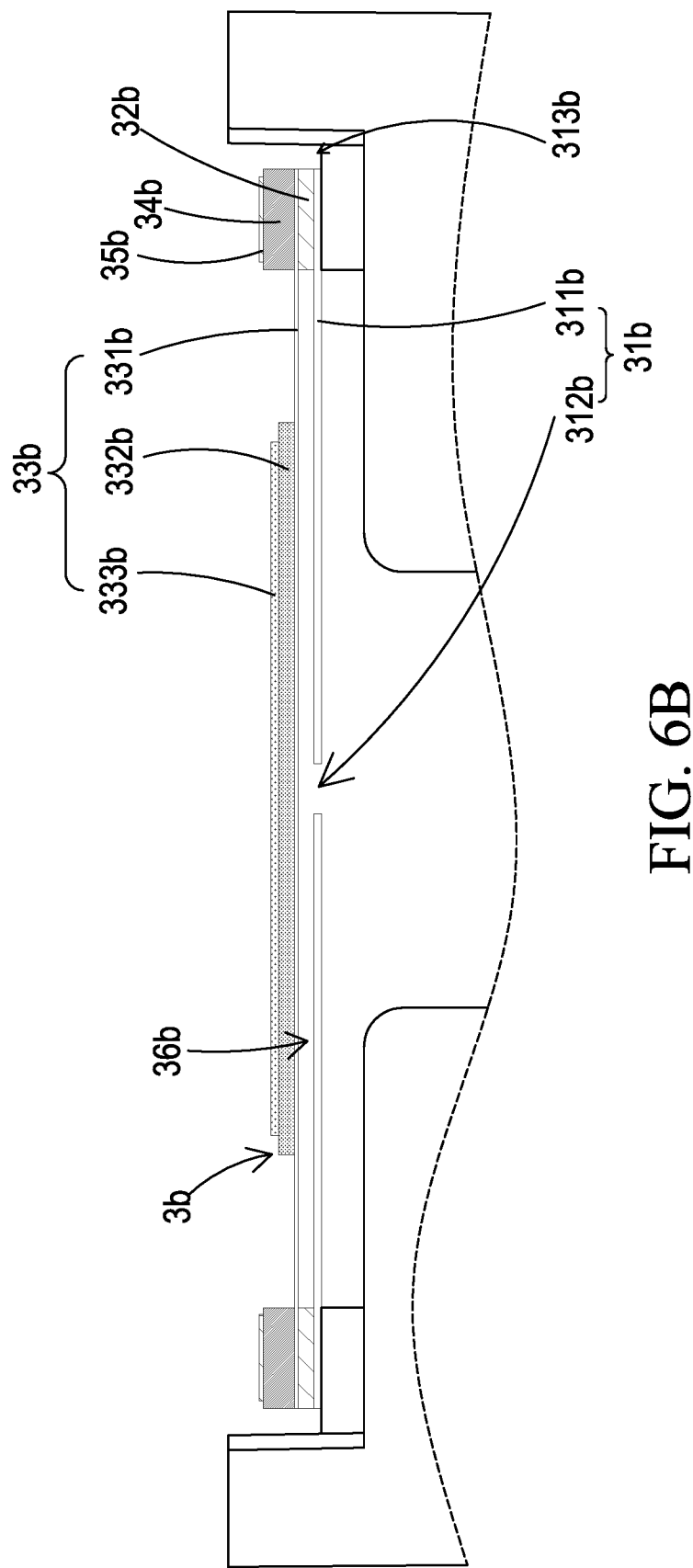
FIG. 6B to FIG. 6D illustrate cross-sectional views showing the operation steps of the piezoelectric blower pump of the miniature gas detection system of the exemplary embodiment in the present disclosure.

Furthermore, the chamber frame 32*b* is stacked on the nozzle plate 31*b*, and the shape of the chamber frame 32*b* is corresponding to the shape of the nozzle plate 31*b*. The actuation body 33*b* is stacked on the chamber frame 32*b*. A resonance chamber 36*b* is collectively defined between the actuation body 32*b*, the nozzle plate 31*b*, and the suspension sheet 311*b* (as shown in FIG. 6B). The insulation frame 34*b* is stacked on the actuation body 34*b*. The appearance of the insulation frame 34*b* is similar to the appearance of the chamber frame 32*b*. The conductive frame 35*b* is stacked on the insulation frame 34*b*. The appearance of the conductive frame 35*b* is similar to the appearance of the insulation frame 34*b*. The conductive frame 35*b* has a conductive pin 351*b* and a conductive electrode 352*b*. The conductive pin 351*b* extends outwardly from the outer edge of the conductive frame 35*b*, and the conductive electrode 352*b* extends inwardly from the inner edge of the conductive frame 35*b*.

Moreover, the actuation body 33*b* further includes a piezoelectric carrying plate 331*b*, an adjusting resonance plate 332*b*, and a piezoelectric plate 333*b*. The piezoelectric carrying plate 331*b* is stacked on the chamber frame 32*b*, and the adjusting resonance plate 332*b* is stacked on the piezoelectric carrying plate 331*b*. The piezoelectric plate 333*b* is stacked on the adjusting resonance plate 332*b*. The adjusting resonance plate 332*b* and the piezoelectric plate 333*b* are accommodated in the insulation frame 34*b*. The conductive electrode 352*b* of the conductive frame 35*b* is electrically connected to the piezoelectric plate 333*b*. In this embodiment, the piezoelectric carrying plate 331*b* and the adjusting resonance plate 332*b* are both made of conductive material(s). The piezoelectric carrying plate 331*b* has a piezoelectric pin 334*b*. The piezoelectric pin 334*b* and the conductive pin 351*b* are in electrical connection with a driving circuit (not shown) of the driving circuit board (not shown) to receive a driving signal (which may be a driving frequency and a driving voltage). The piezoelectric pin 334*b*, the piezoelectric carrying plate 331*b*, the adjusting resonance plate 332*b*, the piezoelectric plate 333*b*, the conductive electrode 352*b*, the conductive frame 35*b*, and the conductive pin 351*b* may together generate an electrical circuit for transmitting the driving signal, and the insulation frame 34*b* is provided for electrically insulating the conductive frame 35*b* from the actuation body 33*b* to avoid short circuit, thereby the driving signal can be transmitted to the piezoelectric plate 333*b*. When the piezoelectric plate 333*b* receives the driving signal, the piezoelectric plate 333*b* deforms owing to the piezoelectric effect, and thus the piezoelectric carrying plate 331*b* and the adjusting resonance plate 332*b* are driven to vibrate reciprocatingly.

Moreover, the adjusting resonance plate 332*b* is disposed between the piezoelectric plate 333*b* and the piezoelectric carrying plate 331*b* as a cushion element so as to adjust the vibration frequency of the piezoelectric carrying plate 331*b*. Generally, the thickness of the adjusting resonance plate 332*b* is greater than the thickness of the piezoelectric carrying plate 331*b*. The thickness of the adjusting resonance plate 331*b* may be modified to adjust the vibration frequency of the actuation body 33*b*. The nozzle plate 31*b*, the chamber frame 32*b*, the actuation body 33*b*, the insulation frame 34*b*, and the conductive frame 35*b* are sequentially stacked and assembled, and a clearance 313*b* is defined outside the suspension sheet 311*b* of the piezoelectric blower pump 3*b* for the air to pass therethrough. A gas flow chamber is formed at the bottom portion of the nozzle plate 31*b*. The gas flow chamber is connected to the resonance chamber 36*b* formed between the actuation body 33*b*, the nozzle plate 31*b*, and the suspension sheet 311*b* through the hollow hole 312*b* of the nozzle plate 31*b*. In this embodiment, the resonance chamber 36*b* and the suspension sheet 311*b* can generate the Helmholtz resonance effect to improve the transmission efficiency of the gas through controlling the vibration frequency of the gas in the resonance chamber 36*b* to be close to the vibration frequency of the suspension sheet 311*b*.

As shown in FIG. 6, when the piezoelectric plate 333*b* moves in a direction away from the bottom of the piezoelectric blower pump 3*b*, the piezoelectric plate 333*b* drives the suspension sheet 331*b* of the nozzle plate 31*b* to move in the direction away from the bottom surface of the piezoelectric blower pump 3*b* correspondingly. Hence, the volume of the gas flow chamber expands dramatically, therefore the internal pressure of the gas flow chamber decreases and creates negative pressure, drawing the air outside the piezoelectric blower pump 3*b* to flow into the piezoelectric blower pump 3*b* through the clearance 313*b* and enter the resonance chamber 36*b* through the hollow hole 312*b*, thereby increasing the gas pressure of the resonance chamber 36*b* and thus generating a pressure gradient.

Figure 6C:
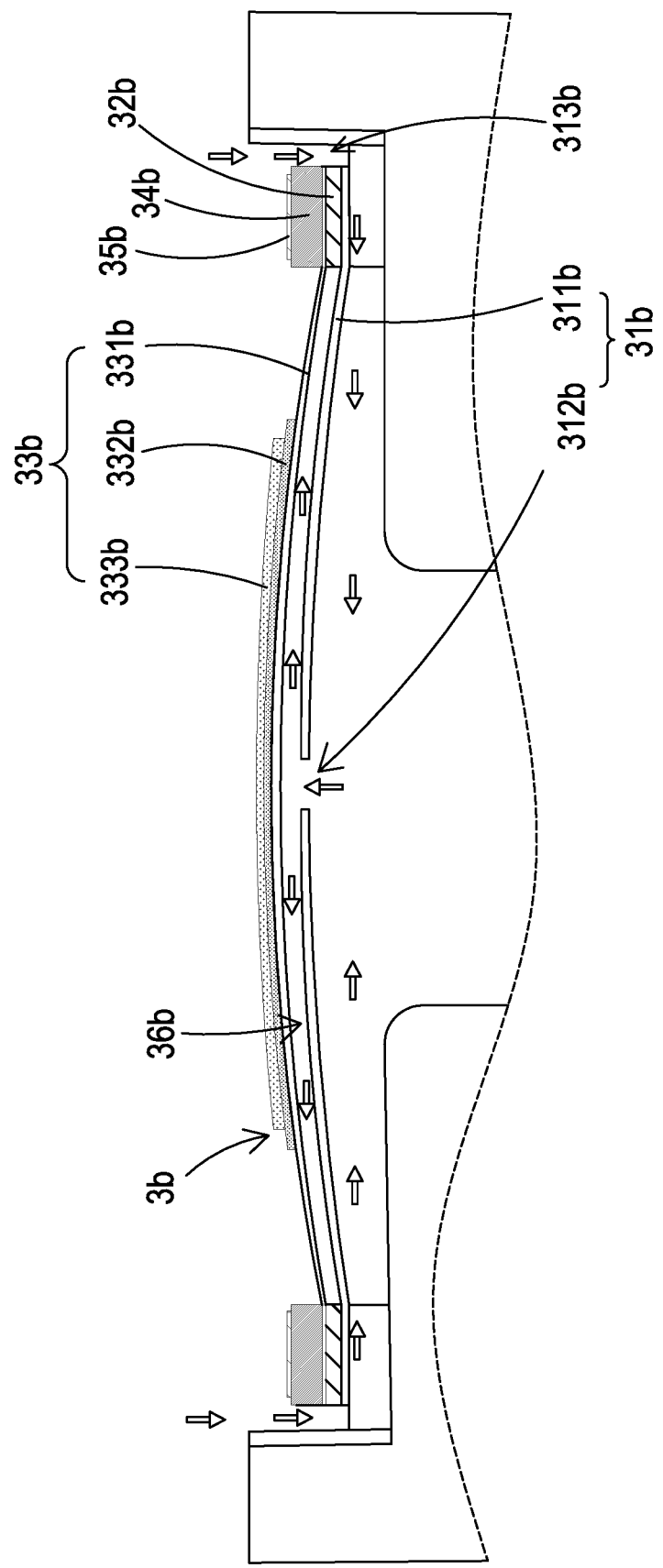
Figure 6D:
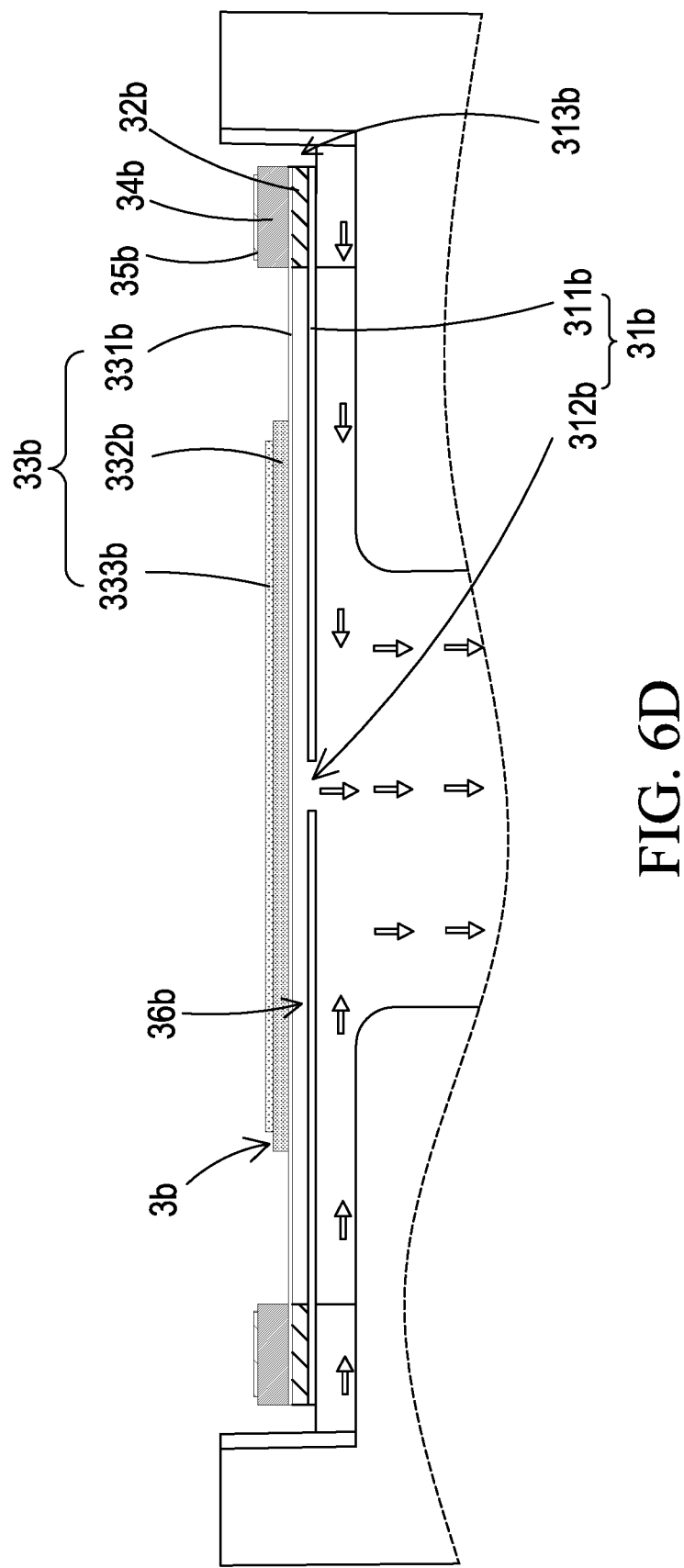

As shown in FIG. 6D, when the piezoelectric plate 333*b* drives the suspension sheet 311*b* of the nozzle plate 31*b* to move toward the bottom surface of the piezoelectric blower pump 3*b*, the gas inside the resonance chamber 36*b* is pushed to flow out quickly through the hollow hole 312*b* to further push the air inside the gas flow chamber, thereby the converged air can be quickly and massively ejected out of the gas flow chamber in a state closing to an ideal gas state under the Benulli's law.

Therefore, through repeating the steps as shown in FIG. 6C and FIG. 6D, the piezoelectric plate 333*b* can bend and vibrate reciprocatingly. Further, after the gas is discharged out of the resonance chamber 36*b*, the internal pressure of the resonance chamber 36*b* is lower than the equilibrium pressure due to the inertia, as a result, the pressure difference guides the gas outside the resonance chamber 36*b* into the resonance chamber 36*b* again. Therefore, through controlling the vibration frequency of the gas in the resonance chamber 36b to be close to the vibration frequency of piezoelectric plate 333b, the resonance chamber 36b and the piezoelectric plate 333b can generate the Helmholtz resonance effect so as to achieve effective, high-speed, and large-volume gas transmission of the air.

Please refer to FIG. 1 and FIG. 7A to FIG. 8C. According to one or some embodiments of the present disclosure, when the MEMS pump 1a of each of the detection flow channels 12 is actuated, the MEMS pump 1a also controls the valve element 4 between the detection flow channel 12 and the main flow channel 11, so that the compositions of compounds at the different regions of the main flow channel 11 are introduced into the monitoring chambers 121 of the respective detection flow channel 12 with the fixed amount, and then the MEMS pump 1a stops operation and controls the valve element 4 between each of the detection flow channels 12 and the main flow channel 11 to be closed. Therefore, in the monitoring chamber 121 of each of the detection flow channels 12, the light emitted from the light emitting element 122 is illuminated on the two mirrors 124, 125, reflected by the two mirrors 124, 125, and received by the light detection element 123, so that the light detection elements 123 obtain and output the spectra of the compositions of compounds contained in the gas according to the differences in optical adsorptions of the compositions of compounds for lights with different wavelengths, so as to analyze and determine the type of the gas contained in the compositions of compounds. In this embodiment, the output pressure of the MEMS pump is 300 mmHg, and the output flow rate of the MEMS pump 1a is 1.5 L/min.

In this embodiment, the MEMS pump 1a includes a first substrate 11a, a first oxide layer 12a, a second substrate 13a, and a piezoelectric element 14a. The first substrate 11a has a plurality of inlets 111a, and each of the inlets 111a is a conical hole. The first oxide layer 12a is stacked on the first substrate, the first oxide layer 12a has a plurality of convergence troughs 121a and a convergence room 122a, and the convergence troughs 121a are in communication between the convergence room 122a and the inlets 111a. The second substrate 13a is combined with the first substrate 11a, and the second substrate 13a includes a silicon wafer layer 131a, a second oxide layer 132a, and a silicon material layer 133a. The silicon wafer layer 131a has an actuation portion 1311a, an outer peripheral portion 1312a, a plurality of connection portions 1313a, and a plurality of fluid channels 1314a. The actuation portion 1311a is of a circular shape. The outer peripheral portion 1312a is of a hollow ring shape and surrounds an outer periphery of the actuation portion 1311a. The connection portions 1313a are respectively connected between the actuation portion 1311a and the outer peripheral portion 1312a. The fluid channels 1314a surround the outer periphery of the actuation portion 1311a and between the connection portions 1313a. The second oxide layer 132a is formed below the silicon wafer layer 131a. The second oxide layer 132a is of a hollow ring shape, and the second oxide layer 132a and the silicon wafer layer 131a together define a gas chamber 1321a. The silicon material layer 133a is of a circular shape, below the second oxide layer 132a, and combined with the first oxide layer 12a. The silicon material layer 133a has a through hole 1331a, a vibration portion 1332a, and a fixed portion 1333a. The through hole 1331a at a central portion of the silicon material layer 133a. The vibration portion 1332a is at a peripheral region of the through hole 1331a. The fixed portion 1333a is at a peripheral region of the silicon material layer 133a. The piezoelectric element 14a is of a circular shape and stacked on the actuation portion 1311a of the silicon wafer layer 131a. The piezoelectric element 14a includes a lower electrode layer 141a, a piezoelectric layer 142a, an insulation layer 143a, and an upper electrode layer 144a. The piezoelectric layer 142a is stacked on the lower electrode layer 141a. The insulation layer 143a is disposed on a part of a surface of the piezoelectric layer 142a and a part of the surface of the lower electrode layer 141a. The upper electrode layer 144a is stacked on the insulation layer 143a and a remaining portion of the surface of the piezoelectric layer 142a where the insulation layer 143a is not disposed, and the upper electrode layer 144a is used for electrically connecting to the piezoelectric layer 142a.

Figure 7A:
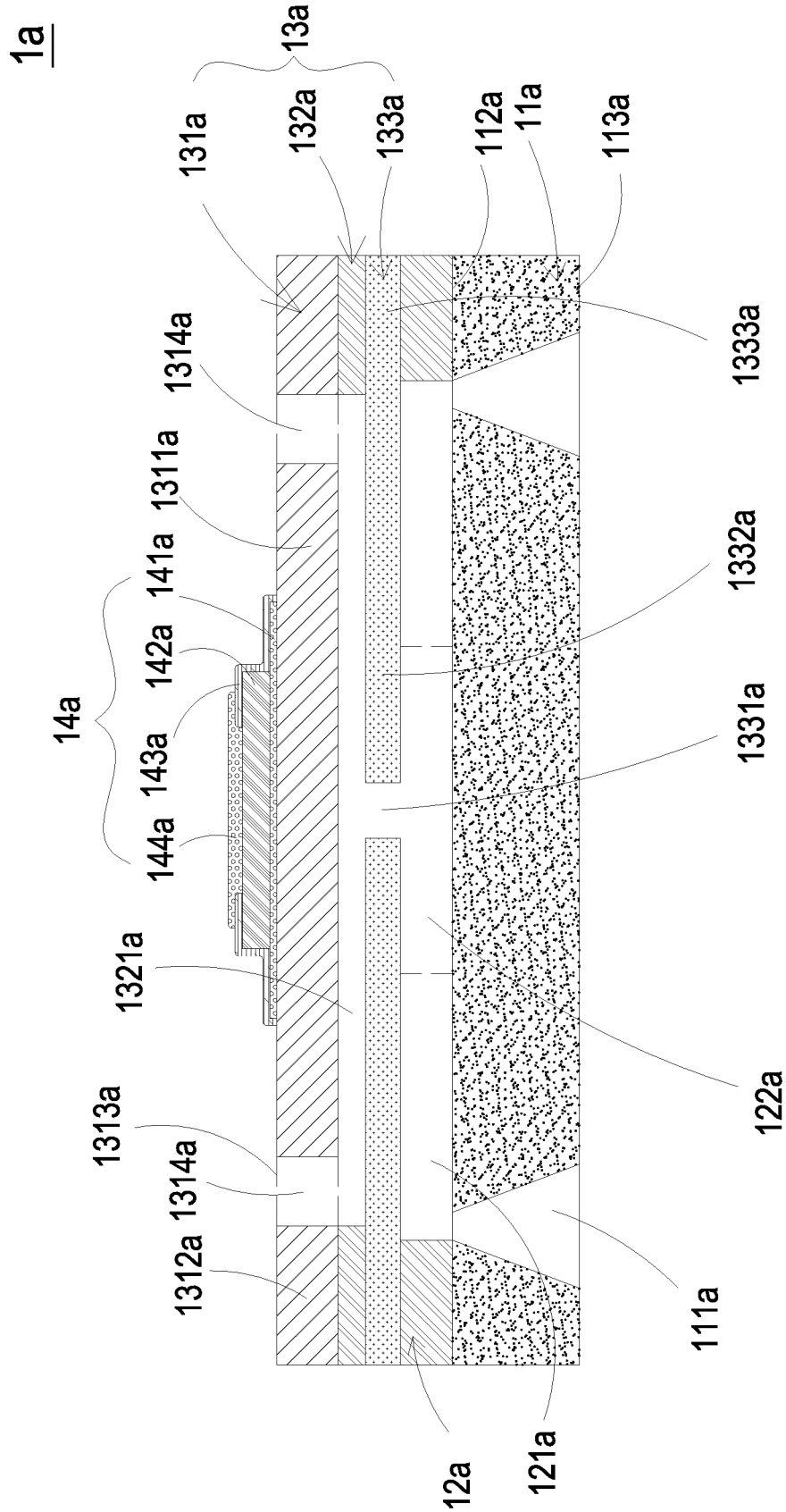
FIG. 7A illustrates a cross-sectional view of a micro-electromechanical systems (MEMS) pump of the miniature gas detection system of the exemplary embodiment in the present disclosure.
Figure 7B:
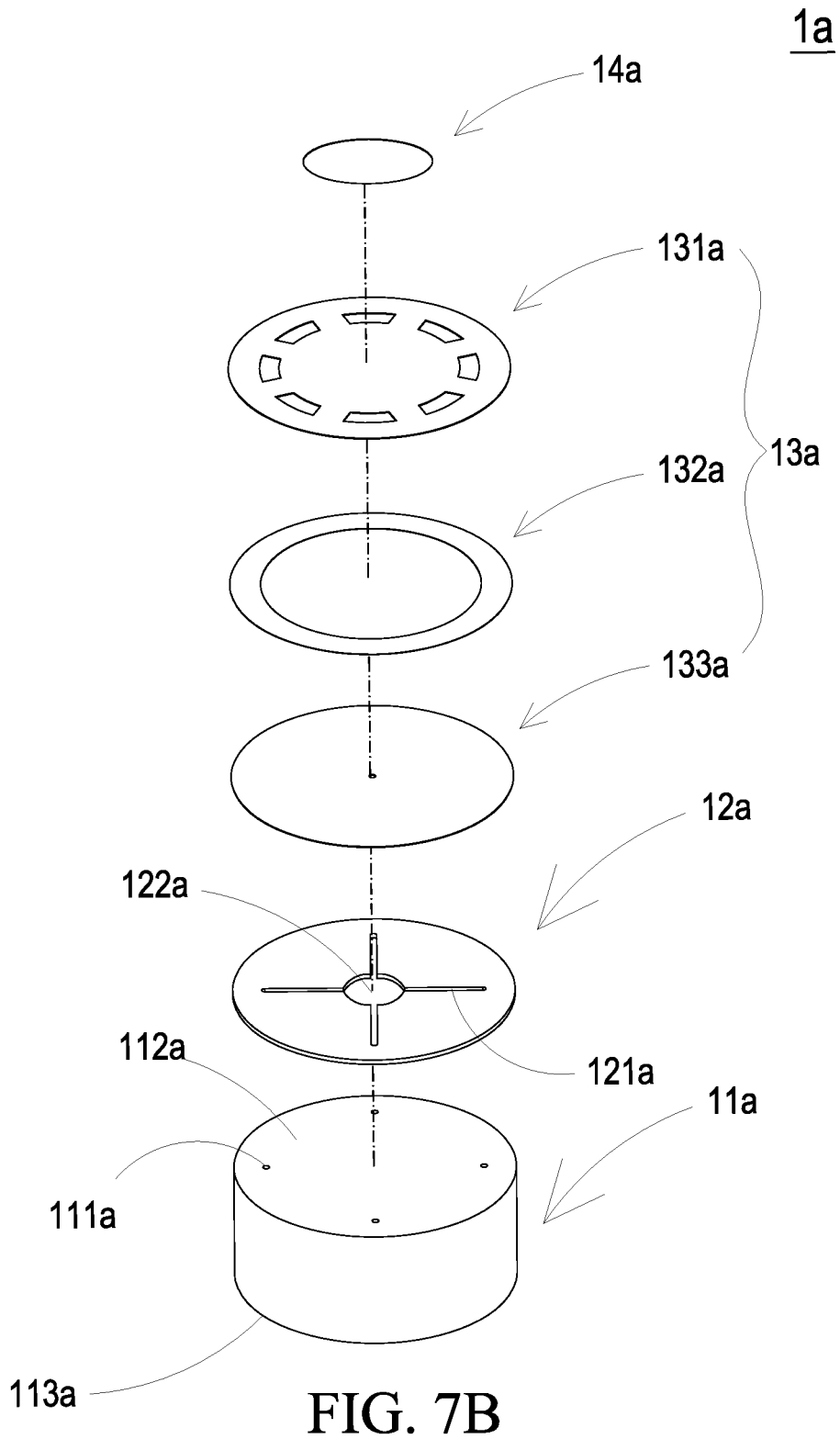
FIG. 7B illustrates an exploded view of the MEMS pump of the miniature gas detection system of the exemplary embodiment in the present disclosure.

Please refer to FIG. 7A and FIG. 7B. FIG. 7A and FIG. 7B illustrate schematic views of the MEMS pump 1a of the exemplary embodiment in the present disclosure. In this embodiment, the MEMS pump 1a includes a first substrate 11a, a first oxide layer 12a, a silicon material layer 133a, a second oxide layer 12a, a silicon wafer layer 131a, and a piezoelectric element 14a sequentially stacked to form the entire structure of the MEMS pump 1a.

The first substrate 11a, the silicon material layer 133a, and the silicon wafer layer 131a may be made of the same material, but not limited thereto. In this embodiment, the first substrate 11a, the silicon material layer 133a, and the silicon wafer layer 131a are silicon chips formed by a crystal growth process of the semiconductor process. The crystal growth process may be a polysilicon growth technique, by which the first substrate 11a, the silicon material layer 133a, and the silicon wafer layer 131a are configured as polysilicon chips. In addition, the first substrate 11a has a first thickness, the silicon material layer 133a has a second thickness, and the silicon wafer layer 131a has a third thickness, wherein the first thickness, the second thickness and the third thickness may be formed by a thinning process. In this embodiment, the first thickness of the first substrate 11a is greater than the third thickness of the silicon wafer layer 131a, and the third thickness of the silicon wafer layer 131a is greater than the second thickness of the silicon material layer 133a. The substrate thinning process may be grinding, etching, cutting, or any other process to achieve the desired thickness of the substrate.

The first oxide layer 12a and the second oxide layer 132a may be both made of the same material, but not limited thereto. In this embodiment, the first oxide layer 12a and the second oxide layer 132a are silicon dioxide ($SiO_2$) films, which can be formed by a sputtering process or high temperature oxidation of the semiconductor procedure, so as to form the films with the desired thickness. In this embodiment, the thickness of the first oxide layer 12a is greater than the thickness of the second oxide layer 132a.

The first substrate 11a has a first top surface 112a, a first bottom surface 113a, and at least one inlet 111a, wherein the first top surface 112a and the first bottom surface 113a both are formed by the crystal growth process of the semiconductor process, and the at least one inlet 111a is formed by a lithography and etching process. Each of the inlet 111a penetrates the first substrate 11a from the first bottom surface 113a to the first top surface 112a. In this embodiment, the number of the inlets 111a is two, but not limited thereto. Moreover, in order to enhance the inhale efficiency, the inlet 111a is of a conical shape and tapered from the first bottom surface 113a to the first top surface 112a.

The first oxide layer 12a is formed and stacked on the first top surface 112a of the first substrate 11a by the sputtering process or high temperature oxidation of the semiconductor procedure. In addition, at least one convergence trough 121a and a convergence room 122a are formed on the first oxide layer 12a by the lithography and etching process. The number and the position of the at least one convergence trough 121a are corresponding to the number and the position of the at least one inlet 111a of the first substrate 11a. In this embodiment, the number of the convergence troughs 121a is two, but not limited thereto. For each of the convergence troughs 121a, one of two ends of the convergence trough 121a is connected to the corresponding inlet 11a, and the other end of the convergence trough 121a is connected to the convergence room 122a. Hence, the gas inhaled from the two inlets 111a can be converged into the convergence room 122a through the corresponding convergence troughs 121a, respectively.

The silicon material layer 133a has a second top surface, a second bottom surface, a vibration portion 1332a, a fixed portion 1333a, and a through hole 1331a wherein the second top surface, the second bottom surface, the vibration portion 1332a, and the fixed portion 1333a are all formed by the crystal growth process of the semiconductor process, and the through hole 1331a is formed by the lithography and etching process. The through hole 1331a is at a central portion of the silicon material layer 133a and penetrates the second top surface and the second bottom surface. The vibration portion is at a peripheral region of the through hole 1331a, and the fixed portion 1333a is at a peripheral region of the vibration portion 1332a. The second bottom surface of the silicon material layer 133a is stacked on the first oxide layer 12a. The through hole 1331a of the silicon material layer 133a is vertically aligned and connected to the convergence room 122a of the first oxide layer 12a, and the through hole 1331a is misaligned with the inlet 111a of the first substrate 11a.

The second oxide layer 132a is formed and stacked on the second top surface of the silicon material layer 133a by the sputtering process or high temperature oxidation of the semiconductor process. A central portion of the second oxide layer 132a is recessed to form a gas chamber 1321a by the lithography and etching process. The gas chamber 1321a is vertically corresponding to the through hole 1331a of the silicon material layer 133a and the vibration portion 1332a at the peripheral region of the through hole 1331a. Therefore, the gas can flow into the gas chamber 1321a by passing though the through hole 1331a, and the vibration portion 1332a can move upward and downward in the gas chamber 1321a.

The silicon wafer layer 131a has a third top surface, a third bottom surface, a plurality of connection portions 1313a, an actuation portion 1311a, an outer peripheral portion 1312a, and a plurality of fluid channels 1314a, wherein the third top surface and the third bottom surface both are formed by the crystal growth process of a semiconductor process, and the connection portions 1313a penetrating the third top surface and the third bottom surface are formed by the lithography and etching process. The actuation portion 1311a is enclosed by the connection portions 1313a, the outer peripheral portion 1312a surrounds an outer periphery of the connection portions 1313a, and the fluid channels 1314a are between the connection portions 1313a and connected between the actuation portion 1311a and the outer peripheral portion 1312a. In this embodiment, the number of the connection portions 1313a is eight, and the number of the fluid channels 1314a is eight as well, but not limited thereto.

Please refer to FIG. 7A again. The piezoelectric element 14a includes a lower electrode layer 141a, a piezoelectric layer 142a, an insulation layer 143a, and an upper electrode layer 144a. The piezoelectric element 14a may be formed by physical vapor deposition (PVD), chemical vapor deposition (CVD) or sol-gel, but not limited thereto. In this embodiment, the upper electrode layer 144a and the lower electrode layer 141a are formed by film deposition such as PVD or CVD. The lower electrode layer 141a is disposed on the third top surface of the silicon wafer layer 131a and on the actuation portion 1311a of the silicon wafer layer 131a. The piezoelectric layer 142a may be formed by film deposition or sol-gel, and the piezoelectric layer 142a is disposed above the lower electrode layer 141a. Hence, the piezoelectric layer 142a and the lower electrode layer 141a can be electrically connected to each other through the contact area. Moreover, the area of the piezoelectric layer 142a is less than the area of the lower electrode layer 141a, so that the lower electrode layer 141a cannot be entirely covered by the piezoelectric layer 142a. Consequently, the insulation layer 143a is formed on a portion of the piezoelectric layer 142a and the uncovered portion of the lower electrode layer 141a (the portion of the lower electrode layer 141a which is not covered by the piezoelectric layer 142a). Then, the upper electrode layer 144a is stacked on a portion of the insulation layer 143a and the uncovered portion of the piezoelectric layer 142a (a remaining portion of the surface of the piezoelectric layer 142a where the insulation layer 143a is not disposed). Accordingly, the upper electrode layer 144a is electrically connected to the piezoelectric layer 142a through the contact area, and the insulation layer 143a prevents the upper electrode layer 144a from directly contacting the lower electrode layer 141a and thus prevents the occurrence of electrical short circuits.

The first oxide layer 12a is between the first top surface 112a of the first substrate 11a and the second bottom surface of the silicon material layer 133a. The second oxide layer 132a is between the second top surface of the silicon material layer 133a and the third bottom surface of the silicon wafer layer 131a. The piezoelectric element 14a is on the third top surface of the silicon wafer layer 131a and corresponding to the second oxide layer 132a which is on the third bottom surface, and the piezoelectric element 14a may be further corresponding to the gas chamber 1321a of the second oxide layer 132a which is on the third bottom surface. Since the first oxide layer 12a is between the first substrate 11a and the silicon material layer 133a, the convergence troughs 121a are connected to the inlets 111a of the first substrate 11a, and the convergence room 122a is connected to the through hole 1331a of the silicon material layer 133a. Therefore, the gas is inhaled from the inlets 111a of the first substrate 11a, converged into the convergence room 122a by passing through the convergence troughs 121a, and then flows upwardly through the through hole 1331a. Moreover, since the second oxide layer 132a is between the silicon material layer 133a and the silicon wafer layer 131a, the gas chamber 1321a is connected to the through hole 1331a of the silicon material layer 133a and the connection portion 1313a of the silicon wafer layer 131a. Consequently, the gas is inhaled into the gas chamber 1321a through the through hole 1331a and then flows out upwardly from the connection portion 1313a, so as to achieve gas transmission.

Figure 8A:
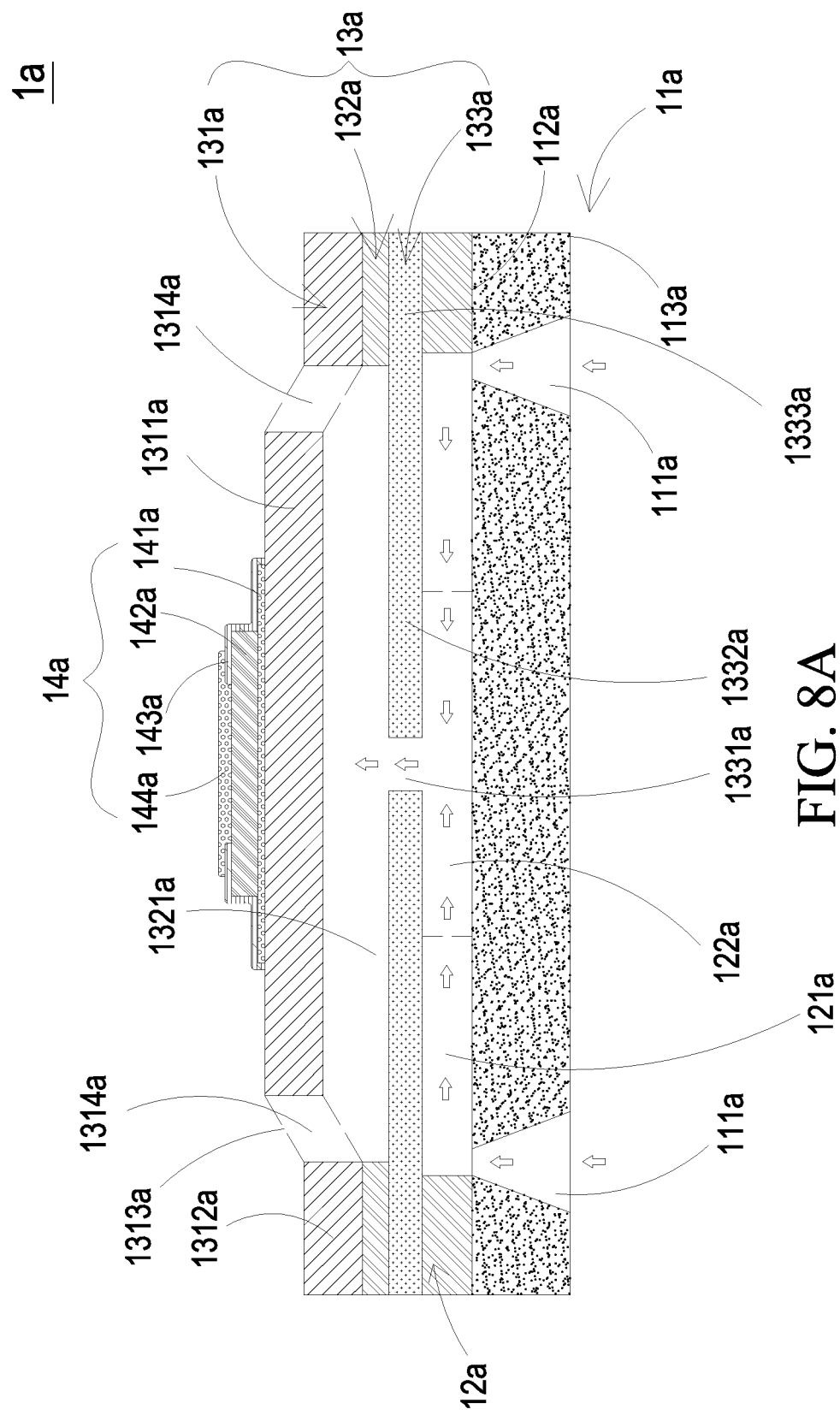
FIG. 8A to FIG. 8C illustrate cross-sectional views showing the operation steps of the MEMS pump of the miniature gas detection system shown in FIG. 7A of the exemplary embodiment in the present disclosure.
Figure 8B:
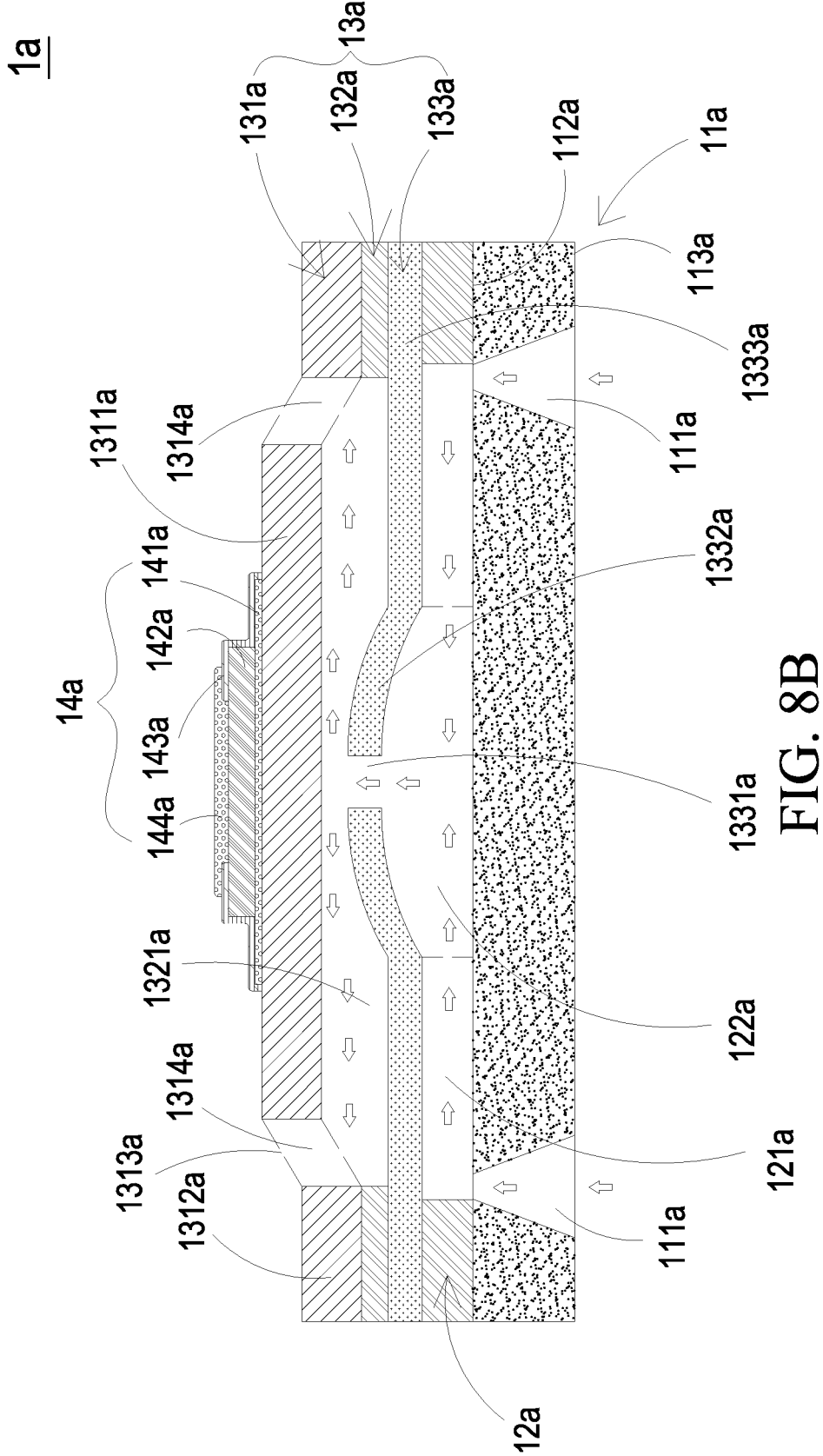
Figure 8C:
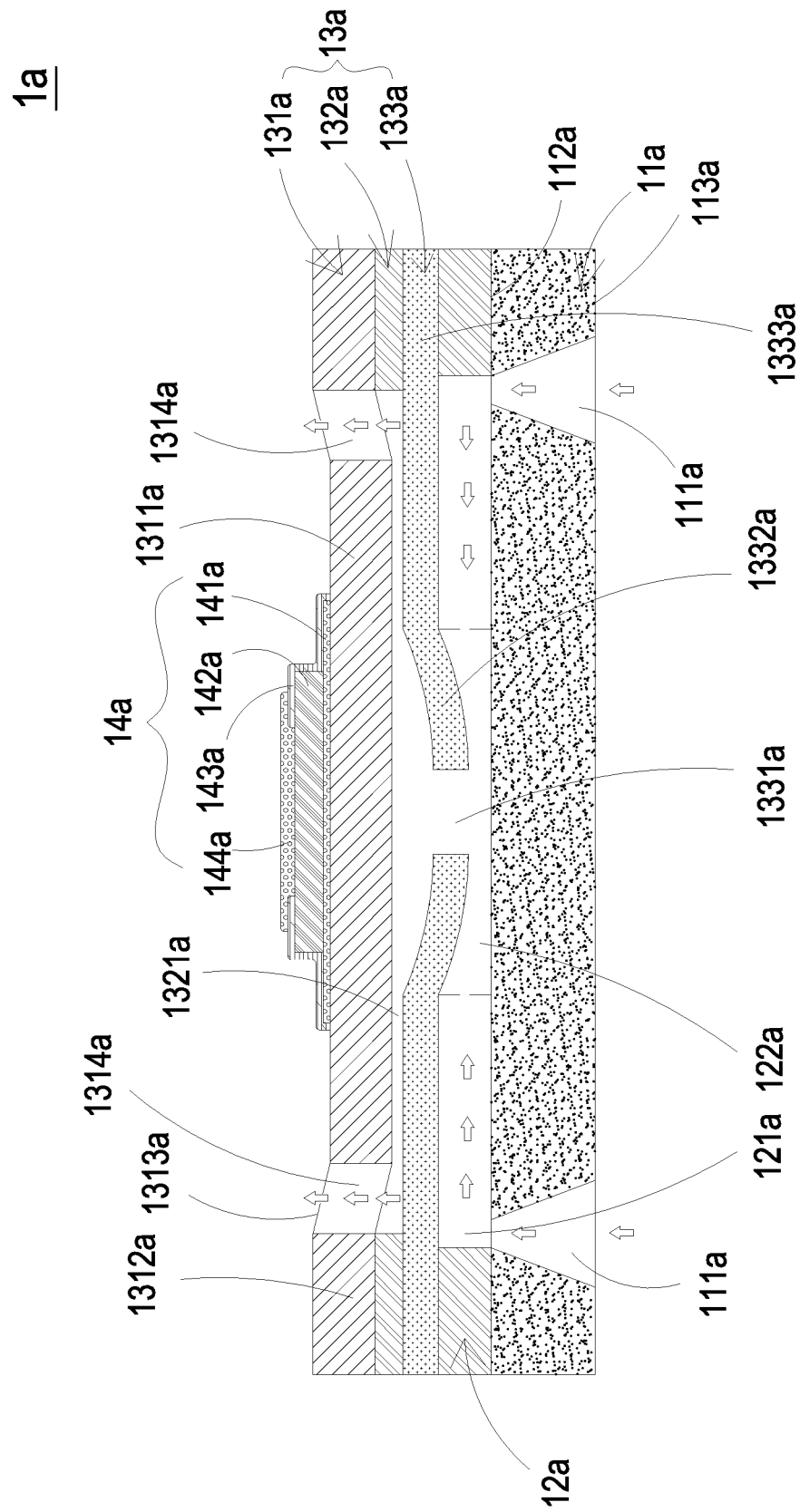

FIG. 8A to FIG. 8C illustrate cross-sectional views showing the operation steps of the MEMS pump which is fabricated by the semiconductor processes of the exemplary embodiment in the present disclosure. As shown in FIG. 8A, when the lower electrode layer 141a and the upper electrode layer 144a of the piezoelectric element 14a receive the voltage and the driving signal (not shown) from the exterior and then transmit to the piezoelectric layer 142a, the piezoelectric layer 142a deforms due to a piezoelectric effect. The variety and frequency of the deformation of the piezoelectric layer 142a are controlled by the voltage and the driving signal. Owing to the deformation of the piezoelectric layer 142a, the actuation portion 1311a of the silicon wafer layer 131a is driven to move upwardly away from the second oxide layer 132a. Since the distance between the actuation portion 1311a and the second oxide layer 132a is increased, the volume of the gas chamber 1321a of the second oxide layer 132a is expanded, and negative pressure is generated in the gas chamber 1321a, so as to inhale the gas outside the MEMS pump 1a into MEMS pump 1a through the inlets 111a, and then converge the gas to the convergence room 122a of the first oxide layer 12a. Then, as shown in FIG. 8B, when the actuation portion 1311a is driven to move upwardly by the piezoelectric element 14a, owing to the resonance effect, the vibration portion 1332a of the silicon material layer 133a also moves upwardly, so as to compress the volume of the gas chamber 1321a. Under this circumstance, the gas in the gas chamber 1321a is pushed toward the connection portion 1313a of the silicon wafer layer 131a, and the gas is then discharged upwardly through the connection portion 1313a. At the same time, when the vibration portion 1332a is moved upwardly to compress the gas chamber 1321a, the volume of the convergence room 122a is expanded in contrast, whereby a negative pressure is also generated in the convergence room 122a and the gas outside the MEMS pump 1a is continuously inhaled into the MEMS pump 1a through the inlets 111a. Finally, as shown in FIG. 8C, when the actuation portion 1311a of the silicon wafer layer 131a is driven to move downwardly by the piezoelectric element 14a, the vibration portion 1332a of the silicon material layer 133a is also driven to move downwardly at the same time. Hence, the vibration portion 1332a compresses the convergence room 122a, and the gas in the convergence room 122a is pushed to move toward the gas chamber 1321a through the through hole 1331a, and the gas outside the MEMS pump 1a temporarily stops inhaling into the MEMS pump 1a through the inlets 111a. At the same time, the gas in the gas chamber 1321a is pushed toward the connection portion 1313a of the silicon wafer layer 131a and discharged outwardly. After that, when the piezoelectric element 14a is resumed to drive the actuation portion 1311a to move upwardly, and the volume of the gas chamber 1321a is increased greatly, so that a higher inhaling force is generated to inhale the gas into the gas chamber 1321a (as shown in FIG. 8A). Through continuously repeating the operation steps shown in FIG. 8A to FIG. 8C, the actuation portion 1311a is driven to move upwardly and downwardly by the piezoelectric element 14a, and the vibration portion 1332a is driven through the resonance effect and is moved, so that the inner pressure of the MEMS pump 1a is continuously changed. As a result, the MEMS pump 1a can perform inhaling and discharging of gas to achieve the gas transmission.

From the above, the miniature gas detection system of one or some embodiments in the present disclosure is fabricated by semiconductor processes, the gas actuator 3 guides the gas into the main flow channel 11 with a stable flow rate, and the detection flow channels 12 are connected to the main flow channel 11, and the gas is transmitted by the MEMS pump 1a and introduced into the monitoring chambers 121 of the detection flow channels 12 through the valve element 4. As shown in FIG. 1, for the gas (which is flowing along the arrow shown in the figure), the compositions of compounds contained in the gas to be detected are adsorbed or separated by the filling material 2 in the main flow channel 11. Because the filling material 2 has different adsorption forces for the compositions of compounds in the gas to be detected, the compositions of compositions of compounds have different flow rates in the main flow channel 11; the compositions of compounds with larger adsorption forces for the filling material 2 have slower flow rates, and the compositions of compounds with smaller adsorption forces for the filling material 2 have faster flow rates. Therefore, when the compositions of compounds contained in the gas to be detected flow in the main flow channel 11, the compositions of compounds are adsorbed by the filling material 2 and thus are separated, so that the compositions of compounds contained in the gas to be detected are presented at different regions of the main flow channel 11 with different flow rates. When the MEMS pump 1a of each of the detection flow channels 12 is actuated, the compositions of compounds at different regions of the main flow channel 11 are introduced into the monitoring chambers 121 of the respective detection flow channels 12 with a fixed amount, and in the monitoring chamber 121 of each of the detection flow channels 12, a light emitted from the light emitting element 122 is illuminated on the two mirrors 124, 125, reflected by the two mirrors 124, 125, and received by the light detection element 123, so that the light detection elements 123 in the respective monitoring chambers 121 obtain and output spectra of the compositions of compounds contained in the gas according to the differences in optical adsorptions of the compositions of compounds for lights with different wavelengths. Then, the external computer system 5 is used to collect the data of spectra of the compositions of compounds outputted by the light detection elements 123 so as to analyze and determine the type of the compositions of compounds contained in the gas. Consequently, according to one or some embodiments of the present disclosure, the separation flow channel 1 of the miniature gas detection system is fabricated by semiconductor processes, and the filling material 2 is disposed in the separation flow channel 1. Hence, the system can be miniaturized and thus can be carried conveniently, can replace the chromatography column in the GC meter, and can be used anytime and anywhere.

Based on the above, according to one or some embodiments of the present disclosure, a miniature gas detection system is provided. In the miniature gas detection system, a separation flow channel is fabricated by semiconductor processes. A filling material is disposed in the separation flow channel. The filling material has different adsorption forces for the compositions of compounds contained in the gas introduced into the separation flow channel; the flow rates of the compositions of compounds with larger adsorption forces for the filling material become slower and slower, while the compositions of compounds with smaller adsorption forces for the filling material tend to have reduced flow rates rarely. Therefore, the difference in the flow rates of the compositions of compounds allows the compositions of compounds to be separated at different regions of the separation flow channel, thereby achieving the gas chromatography purpose. Moreover, a plurality of detection flow channels is disposed in parallel in the separation flow channel, and each of the detection flow channels has a monitoring chamber and is cooperated with a valve element and a MEMS pump. Therefore, the compositions of compounds at different regions of the main flow channel are introduced into the monitoring chambers of the respective detection flow channels with a fixed amount when the MEMS pumps are actuated. In the monitoring chamber of each of the detection flow channels, a light emitted from the light emitting element is illuminated on the two mirrors, reflected by the two mirrors, and received by the light detection element, so that the light detection elements in the respective monitoring chambers obtain and output spectra of the compositions of compounds contained in the gas according to the differences in optical adsorptions of the compositions of compounds for lights with different wavelengths, so as to analyze and determine the type of the gas contained in the compositions of compounds. Hence, the system can be miniaturized and thus can be carried conveniently, can replace the chromatography column in the GC meter, and can be used anytime and anywhere.

The foregoing outlines feature of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A miniature gas detection system comprising:
   a separation flow channel fabricated by semiconductor processes, wherein the separation flow channel comprises a main flow channel and a plurality of detection flow channels; the main flow channel guides a gas for detection, and the detection flow channels are connected to the main flow channel; each of the detection flow channels is formed with a monitoring chamber, a light emitting element is on one side of the monitoring chamber, and a light detection element is stacked and positioned on the light emitting element; two mirrors are formed on two sides of the monitoring chamber and corresponding to each other; a micro-electromechanical systems (MEMS) pump is formed on a bottom portion of the monitoring chamber;
   a filling material disposed in the main flow channel of the separation flow channel to perform adsorption and separation on compositions of compounds contained in the gas introduced into the main flow channel;
   wherein the compositions of compounds contained in the gas introduced into the main flow channel are adsorbed or separated by the filling material and presented at different regions of the main flow channel with different flow rates; when the MEMS pump of each of the detection flow channels is actuated, the compositions of compounds at different regions of the main flow channel are introduced into the monitoring chambers of the respective detection flow channels with a fixed amount, and in the monitoring chamber of each of the detection flow channels, a light emitted from the light emitting element is illuminated on the two mirrors, reflected by the two mirrors, and received by the light detection element, so that the light detection elements in the respective monitoring chambers obtain and output spectra of the compositions of compounds contained in the gas according to the differences in optical adsorptions of the compositions of compounds for lights with different wavelengths, so as to analyze and determine the type of the gas contained in the compositions of compounds.

2. The miniature gas detection system according to claim 1, further comprises a gas actuator, wherein the gas actuator is a small piezoelectric pump connected to the main flow channel, the gas actuator is actuated to guide the gas into the main flow channel with a stable flow rate, so that the filling material performs adsorption and separation on the compositions of compounds contained in the gas.

3. The miniature gas detection system according to claim 2, wherein the piezoelectric pump comprises:
   an inlet plate having at least one inlet hole, at least one convergence channel, and a convergence chamber, wherein the at least one inlet hole is used to introduce the gas into the piezoelectric pump, the at least one inlet hole correspondingly penetrates into the at least one convergence channel, and the at least one convergence channel is converged into the convergence chamber, so that the gas introduced from the at least one inlet hole is converged into the convergence chamber;
   a resonance sheet attached to the inlet plate, wherein the resonance sheet has a perforation, a movable portion, and a fixed portion; the perforation is located at a central portion of the resonance sheet and corresponding to the convergence chamber of the inlet plate, the movable portion is disposed at a periphery of the perforation and is disposed at a portion corresponding to the convergence chamber, and the fixed portion is disposed at an outer periphery of the resonance sheet and attached to the inlet plate; and
   a piezoelectric actuator attached to the resonance sheet and disposed correspondingly to the resonance sheet, wherein the piezoelectric actuator comprises a suspension plate, an outer frame, at least one supporting element, and a piezoelectric element; the suspension plate is of a square shape and capable of bending and vibrating; the outer frame is disposed around a periphery of the suspension plate; the at least one supporting element is formed between the suspension plate and the outer frame to provide a flexible support for the suspension plate; the piezoelectric element has a side length, the side length of the piezoelectric element is smaller than or equal to a side length of the suspension plate, and the piezoelectric element is attached to a surface of the suspension plate so as to drive the suspension plate to bend and vibrate when the piezoelectric element is applied with a voltage;
   wherein a chamber space is between the resonance sheet and the piezoelectric actuator, so that when the piezoelectric actuator is driven, the gas outside the piezoelectric pump is introduced into the piezoelectric pump through the at least one inlet hole of the inlet plate, converged into the convergence chamber via the at least one convergence channel, flowed through the perforation of the resonance sheet, and transmitted outwardly by a resonance effect resulting between the piezoelectric actuator and the movable portion of the resonance sheet.

4. The miniature gas detection system according to claim 3, wherein the piezoelectric pump further comprises a first insulation sheet, a conductive sheet, and a second insulation sheet; the inlet plate, the resonance sheet, the piezoelectric actuator, the first insulation sheet, the conductive sheet, and the second insulation sheet are sequentially stacked and assembled.

5. The miniature gas detection system according to claim 2, wherein the gas actuator is a piezoelectric blower pump, and the piezoelectric blower pump comprises:

a nozzle plate comprising a suspension sheet and a hollow hole, wherein the suspension sheet is capable of bending and vibrating, and the hollow hole is formed at a central portion of the suspension sheet;

a chamber frame stacked on the suspension sheet;

an actuation body stacked on the chamber frame, wherein the actuation body comprises a piezoelectric carrying plate, an adjusting resonance plate, and a piezoelectric plate; the piezoelectric carrying plate is stacked on the chamber frame, the adjusting resonance plate is stacked on the piezoelectric carrying plate, and the piezoelectric plate is stacked on the adjusting resonance plate so as to drive the piezoelectric carrying plate and the adjusting resonance plate to bend and vibrate reciprocatingly when the piezoelectric plate is applied with a voltage;

an insulation frame stacked on the actuation body; and a conductive frame stacked on the insulation frame;

wherein the nozzle plate is fixed, so that a clearance is defined outside the nozzle plate for the gas to flow therethrough; a gas flow chamber is formed at a bottom portion of the nozzle plate, and a resonance chamber is formed among the actuation body, the chamber frame, and the suspension sheet; the nozzle plate is capable of being driven to move correspondingly by driving the actuation body, so that the suspension sheet of the nozzle plate vibrates reciprocatingly, and thus the gas enters the gas flow chamber through the gap and then is discharged out of the gas flow chamber, thereby achieving a gas transmission.

6. The miniature gas detection system according to claim 1, wherein the filling material is a porous polymer that is adsorptive, a molecular sieve material that is adsorptive, or a combination thereof, and the filling material is filled in the main flow channel.

7. The miniature gas detection system according to claim 1, wherein the filling material is a filling substrate uniformly covered by a fixed liquid film which is adsorptive, and the filling material is filled in the main flow channel.

8. The miniature gas detection system according to claim 1, wherein the filling material is an oxide of silicon, and a surface of the filling material has hydroxyl groups for implanting the fixed liquid film on the surface of the filling material.

9. The miniature gas detection system according to claim 1, wherein the filling material is a fixed liquid film directly coated on an inner surface of the main flow channel.

10. The miniature gas detection system according to claim 1, wherein the filling material is a fixed liquid film directly sputtered on an inner surface of the main flow channel.

11. The miniature gas detection system according to claim 1, wherein a valve element is formed at a communication portion between each of the detection flow channels and the main flow channel.

12. The miniature gas detection system according to claim 11, wherein the valve element comprises an upper base layer, a lower base layer, and a valve layer; the valve layer is in a receiving space between the upper base layer and the lower base layer, a plurality of ventilation holes is respectively formed on the upper base layer, the lower base layer, and the valve layer; the ventilation holes of the upper base layer and the ventilation holes of the valve layer are substantially aligned with each other, and the ventilation holes of the lower base layer and the ventilation holes of the upper base layer are not aligned with each other; the valve layer is a charged material, and the upper base layer is a conductive material with bipolarity; when the valve layer and the upper base layer are of different polarities, the valve layer is moved toward the upper base layer, so that the valve element is opened; when the valve layer and the upper base layer are of the same polarity, the valve layer is moved toward the lower base layer, so that the valve element is closed.

13. The miniature gas detection system according to claim 11, wherein when the MEMS pump of each of the detection flow channels is actuated, the MEMS pump also controls the valve element between the detection flow channel and the main flow channel, so that the compositions of compounds at the different regions of the main flow channel are introduced into the monitoring chambers of the respective detection flow channel with the fixed amount, and then the MEMS pump stops operation and controls the valve element between each of the detection flow channels and the main flow channel to be closed, therefore in the monitoring chamber of each of the detection flow channels, the light emitted from the light emitting element is illuminated on the two mirrors, reflected by the two mirrors, and received by the light detection element, so that the light detection elements obtain and output the spectra of the compositions of compounds contained in the gas according to the differences in optical adsorptions of the compositions of compounds for lights with different wavelengths, so as to analyze and determine the type of the gas contained in the compositions of compounds.

14. The miniature gas detection system according to claim 11, wherein data of the spectra of the compositions of compounds received and obtained by the light detection elements are outputted to an external computer system, so that the external computer system performs data capture, data storage, and data analysis on the data of the spectra, so as to analyze and determine the type of the gas contained in the compositions of compounds.

15. The miniature gas detection system according to claim 1, wherein the MEMS pump comprises:
a first substrate having a plurality of inlets, wherein each of the inlets is a conical hole;
a first oxide layer stacked on the first substrate, wherein the first oxide layer has a plurality of convergence troughs and a convergence room, and the convergence troughs are in communication between the convergence room and the inlets;
a second substrate combined with the first substrate, comprising:
a silicon wafer layer, having:
an actuation portion being of a circular shape;
an outer peripheral portion being of a hollow ring shape and surrounding an outer periphery of the actuation portion;
a plurality of connection portions respectively connected between the actuation portion and the outer peripheral portion; and
a plurality of fluid channels surrounding the outer periphery of the actuation portion and between the connection portions;
a second oxide layer formed below the silicon wafer layer, wherein the second oxide layer is of a hollow ring shape, and the second oxide layer and the silicon wafer layer together define a gas chamber; and
a silicon material layer being of a circular shape and below the second oxide layer, wherein the silicon material layer is combined with the first oxide layer, and the silicon material layer has:
a through hole at a central portion of the silicon material layer;

a vibration portion at a peripheral region of the through hole; and a fixed portion at a peripheral region of the silicon material layer; and a piezoelectric element being of a circular shape and stacked on the actuation portion of the silicon wafer layer.

16. The miniature gas detection system according to claim 15, wherein the piezoelectric element comprises:

a lower electrode layer;

a piezoelectric layer stacked on the lower electrode layer;

an insulation layer disposed on a part of a surface of the piezoelectric layer and a part of a surface of the lower electrode layer; and an upper electrode layer stacked on the insulation layer and a remaining portion of the surface of the piezoelectric layer where the insulation layer is not disposed, wherein the upper electrode layer is used for electrically connecting to the piezoelectric layer.

17. The miniature gas detection system according to claim 1, wherein a length of the main flow channel is in a range between 2 mm and 24 mm, a length of each of the monitoring chambers connected to the main flow channel is in a range between 0.8 mm and 2 mm, the number of the monitoring chambers is in a range between 1 and 30, and the number of the MEMS pumps is in a range between 1 and 30.

18. The miniature gas detection system according to claim 1, wherein the length of the main flow channel is in a range between 2 μm and 24 μm, the length of each of the monitoring chambers connected to the main flow channel is in a range between 800 nm and 2 μm, the number of the monitoring chambers is in a range between 1 and 30, and the number of the MEMS pumps is in a range between 1 and 30.

19. The miniature gas detection system according to claim 1, wherein an output pressure of the MEMS pump is 300 mmHg, and an output flow rate of the MEMS pump is 1.5 L/min.

* * * * *